US007034036B2

(12) United States Patent
Schoenhard

(10) Patent No.: US 7,034,036 B2
(45) Date of Patent: Apr. 25, 2006

(54) INHIBITORS OF ABC DRUG TRANSPORTERS AT THE BLOOD-BRAIN BARRIER

(75) Inventor: Grant L. Schoenhard, San Carlos, CA (US)

(73) Assignee: Pain Therapeutics, Inc., South San Francisco, CA (US)

( * ) Notice: Subject to any disclaimer, the term of this patent is extended or adjusted under 35 U.S.C. 154(b) by 0 days.

(21) Appl. No.: 10/000,113

(22) Filed: Oct. 30, 2001

(65) Prior Publication Data

US 2003/0073713 A1 Apr. 17, 2003

Related U.S. Application Data

(60) Provisional application No. 60/244,482, filed on Oct. 30, 2000, provisional application No. 60/245,110, filed on Nov. 1, 2000, and provisional application No. 60/246,235, filed on Nov. 2, 2000.

(51) Int. Cl.
*A61K 31/44* (2006.01)
*A61K 31/52* (2006.01)
*A61K 31/445* (2006.01)

(52) U.S. Cl. .................. 514/282; 514/253; 514/321; 514/649; 514/651

(58) Field of Classification Search .......... 514/282, 514/651, 253, 321, 649, 659, 677
See application file for complete search history.

(56) References Cited

U.S. PATENT DOCUMENTS

| | | | | | |
|---|---|---|---|---|---|
| 4,774,230 | A | * | 9/1988 | Tuttle et al. | 514/27 |
| 4,873,076 | A | * | 10/1989 | Fishman et al. | 514/220 |
| 5,512,593 | A | * | 4/1996 | Dante | 514/410 |
| 5,580,876 | A | * | 12/1996 | Crain et al. | 514/282 |
| 5,767,125 | A | * | 6/1998 | Crain et al. | 514/282 |
| 5,817,665 | A | * | 10/1998 | Dante | 514/282 |
| 5,945,510 | A | * | 8/1999 | Fasano | 530/350 |
| 5,958,962 | A | * | 9/1999 | Cook | 514/397 |
| 6,034,091 | A | * | 3/2000 | Dante | 514/282 |
| 6,120,806 | A | * | 9/2000 | Whitmire | 424/497 |
| 6,153,621 | A | * | 11/2000 | Hamann | 514/282 |
| 6,228,863 | B1 | * | 5/2001 | Palermo et al. | 514/282 |
| 6,271,240 | B1 | * | 8/2001 | Simon | 514/282 |
| 6,277,384 | B1 | * | 8/2001 | Kaiko et al. | 424/400 |
| 6,284,765 | B1 | * | 9/2001 | Caffrey | 514/263.32 |
| 6,323,236 | B1 | * | 11/2001 | McElroy | 514/439 |
| 6,622,036 | B1 | * | 9/2003 | Suffin | 600/544 |
| 2002/0044968 | A1 | * | 4/2002 | van Lengerich | 424/469 |
| 2003/0148941 | A1 | * | 8/2003 | Crain et al. | 514/12 |

OTHER PUBLICATIONS

Boström, Emma, et al., "Oxycodone Pharmacokinetics and Pharmacodynamics in the Rat in the Presence of the P–Glycoprotein Inhibitor PSC833," Journal of Pharmaceutical Sciences, vol. 94, No. May 2005 (1060–66).

Zhen–Li Liu, et al., "Persistent reversal of P–glycoprotein–mediated daunorubicin resistance by tetrandrine in multi-drug–resistant human T lymphoblasted leukemia MOLT–4 cells,"*Journal of Controlled Release*,78:43–54 (2002).
Hiroyuki Kushhara, et al., "Role of transporters in the tissue–selective distribution and elimination of drugs: transporters in the liver, small intestine, brain and kidney,"*Journal of Controlled Release*,78:43–54 (2002).
Editorial, "Membrane Transporters,"*European Journal of Pharmaceutical Sciences*,21:1 (2004).
Haiyung Sun, et al. "Drug efflux transporters in the CNS, "*Advanced Drug Delivery Reviews*,55:83–105 (2003).
Richard B. Kim, "Pharmacogenetics of CYP enzymes and drug transporters: remarkable recent advances,"*Advanced Drug Delivery Reviews*,54:1241–1242 (2002).
Tetsuya Terasaki, et al., "The Blood–brain barrier efflux transporters as a detoxifying system for the brain,"*Advanced Drug Delivery Reviews*,36:195–209 (1999).
Akira Tsuji, et al., "Carrier–mediated or specialized transport of drugs across the blood–brain barrier,"*Advanced Drug Delivery Reviews*,36:277–290 (1999).
Massimo Rizzi, et al., "Limbic Seizures Induce P–Glycoprotein in Rodent Brain: Functional Implications for Pharmacoresistance,"*The Journal of Neuroscience*, 22(14):5833–5839 (Jul. 15, 2002).
Astrid A. Ruefli, et al., "HMBA induces activation of a caspase–independent cell death pathway to overcome P–glycoprotein–mediated multidrug resistance,"*Blood*,vol. 95, No. 7, 2378–2385 (Apr. 1, 2000).
Mark J. Smyth, et al., "The drug efflux protein, P–glycoprotein, additionally protects drug–resistant tumor cells from multiple forms of casepase–dependent apoptosis, "*Proc. Natl. Acad. Sci. USA*,vol. 95:7024–7029 (Jun. 1998).
Miki Susanto, et al., "Can the Enhanced Renal Clearance of Antibodies in Cystic Fibrosis Patients be Explained by P–Glycoprotein Transport?,"*Pharmaceutical Research*,vol. 19, No. 4, 457–462 (Apr. 2002).
Seong Hoon Jang, et al., "Kinetics of P–Glycoprotein–Mediated Efflux of Paclitaxel,"*The Journal of Pharmacology and Experimental Therapeutics*,vol. 298, No. 3, 1236–1242 (2001).
Ricky W. Johnstone, et al., "P–Glycoprotein Does Not Protect Cells against Cytolysis Induced by Pore–forming Proteins,"*The Journal of Biological Chemistry*,vol. 276, No. 20, 16667–16673 (May 18, 2001).

(Continued)

Primary Examiner—Vickie Kim
(74) Attorney, Agent, or Firm—McAndrews, Held & Malloy, Ltd.

(57) ABSTRACT

The present invention relates to inhibitors of drug transporters of the ABC protein superfamily, particularly transporters present at the blood brain barrier. ABC transporter inhibitors identified according to the invention increase brain concentrations of CNS-active agents. Such inhibitors increase the influx into the brain and/or reduce the efflux from the brain of such CNS-active agents.

10 Claims, 40 Drawing Sheets

OTHER PUBLICATIONS

Ricky W. Johnstone, et al., "A Role for P–Glycoprotein in Regulating Cell Death,"*Leukemia and Lymphoma,* vol. 38(1–2), 1–11 (2000).

Ricky W. Johnstone, et al., "P–Glycoprotein Protects Leukemia Cells Against Caspase–Dependent, but not Caspase–Independent, Cell Death,"*Blood,*vol. 93, No. 3, 1075–1085 (Feb. 1, 1999).

Richard B. Kim, "Drugs As P–Glycoprotein Substrates, Inhibitors, and Inducers,"*Drug Metabolism Reviews,* 34(1&2), 47–54 (2002).

Pamela L. Golden, et al., "Brain Microvascular P–Glycoprotein and a Revised Model of Multidrug Resistance in Brain,"*Cellular and Molecular Neurobiology,*vol. 20, No. 2, 165–181 (2000).

Hirofumi Hamada, et al., "Characterization of the ATPase Activity of the $M_r$ 170,000 to 180,000 Membrane Glycoprotein (P–Glycoprotein) Associated with Multidrug Resistance in K562/ADM Cells,"*Cancer Research,*48:4926–4932 (Sep. 1, 1988).

Donna S. Cox, et al., "Influence of multidrug resistance (MDR) proteins at the blood–brain barrier on the transporter distribution of enaminone anticonvulsants,"*J. Pharm. Sci.,* vol. 90, No. 10, pp. 1540–1552.

A. H. Dantzig, et al., "Considerations in the design and development of transport inhibitors as adjuncts to drug, "*Advanced Drug Delivery Reviews,*vol. 55, No. 1, pages 133–150 (2003).

A. H. Dantzig, et al., "Evaluation of the binding of the tricyclic isoxazole photoaffinity label LY475776 to multidrug resistance associated protein 1 (mrpl) orthologs and several ATP–binding cassette (ABC transporters),"*Biochemical Pharmacology,*vol. 67, No. 6, pp. 1111–1121 (2004).

T.R. Slouch, "Progress in understanding the structure–activity relationships of p–glycoprotein,"*Advanced Drug Delivery Reviews,*vol. 54, No. 3, pp. 315–328 (2002).

A.H. Schinkel, "Mammalian drug efflux transporters of the ATP binding cassette (ABC) family: an overview,"*Advanced Drug Delivery Reviews,*vol. 55, No. 1, pp. 3–29 (2003).

Pamela L. Golden, et al., "Blood–Brain Barrier Efflux Transport,"*Journal of Pharmaceutical Sciences,*vol. 92, No. 9, 1739–1753 (Sep. 2003).

* cited by examiner

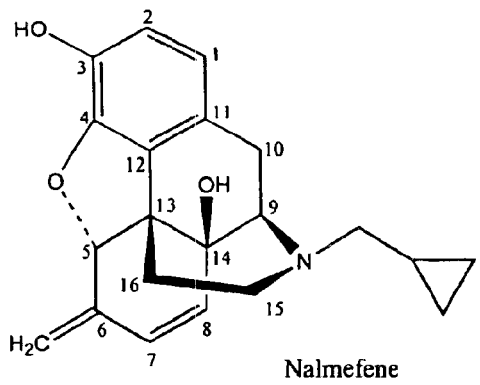
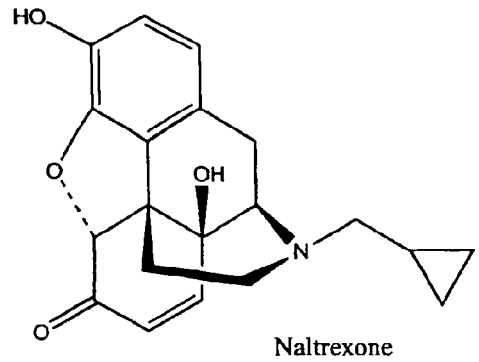
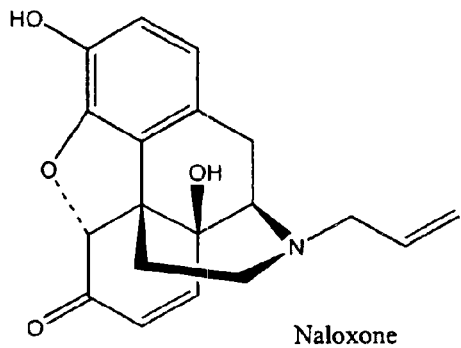
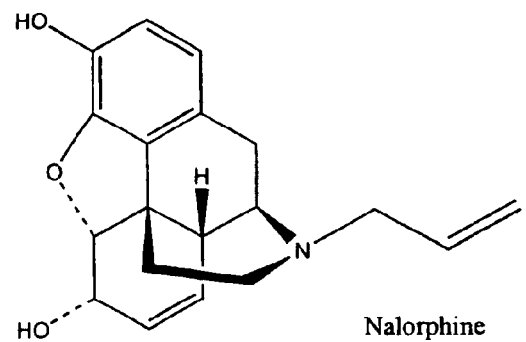
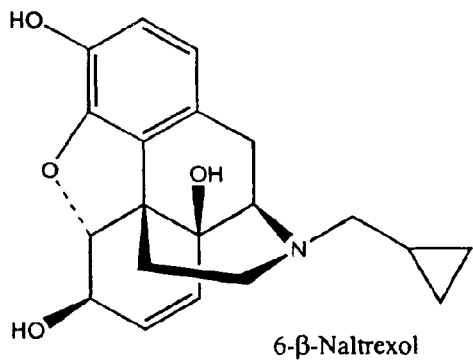
FIG. 1

200 Neighbors

| Structure | Cpd ID | | MW | Distance | Neighbor |
|---|---|---|---|---|---|
| 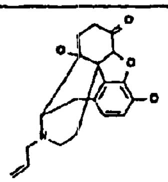 | 70413 | $C_{19}H_{21}NO_4$ | 327.384 | 0.010 | Naloxone |
| 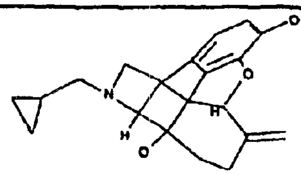 | MFCD00133650 | $C_{21}H_{25}NO_3$ | 339.438 | 0.018 | Nalmefene |
| 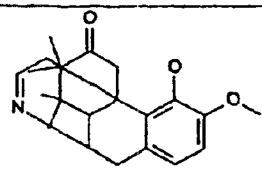 | 349115 | $C_{21}H_{27}NO_3$ | 341.454 | 0.406 | Nalmefene |
| 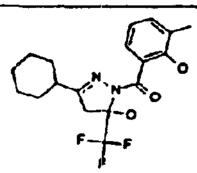 | BAS 3387173 | $C_{18}H_{21}F_3N_2O_3$ | 370.375 | 0.510 | Naloxone |
| 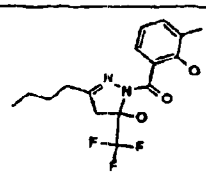 | BAS 1002455 | $C_{16}H_{19}F_3N_2O_3$ | 344.337 | 0.519 | Naloxone |
| 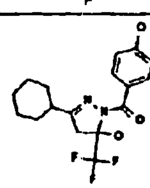 | BAS 3387155 | $C_{17}H_{19}F_3N_2O_3$ | 356.348 | 0.524 | Naloxone |
| | | | | | |

Fig. 4A

200 Neighbors

| Structure | Cpd ID | | MW | Distance | Neighbor |
|---|---|---|---|---|---|
| 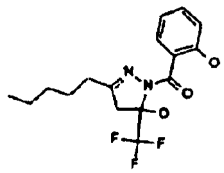 | BAS 1268016 | $C_{16}H_{19}F_3N_2O_3$ | 344.337 | 0.534 | Naloxone |
| 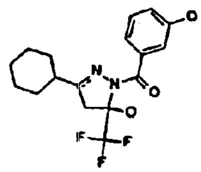 | BAS 3387156 | $C_{17}H_{19}F_3N_2O_3$ | 358.348 | 0.541 | Naloxone |
| 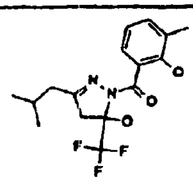 | BAS 3387130 | $C_{16}H_{19}F_3N_2O_3$ | 344.337 | 0.546 | Naloxone |
| 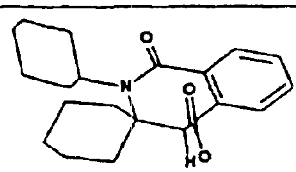 | MFCD01935543 | $C_{21}H_{27}NO_3$ | 341.454 | 0.551 | Naloxone |
| 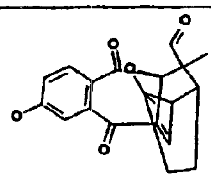 | 688277 | $C_{20}H_{18}O_5$ | 338.363 | 0.591 | 6-beta-Naltrexol |
| 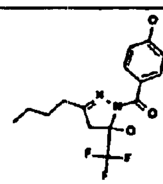 | BAS 1002441 | $C_{15}H_{17}F_3N_2O_3$ | 330.310 | 0.618 | Naloxone |

Fig. 4B

200 Neighbors
| Structure | Cpd ID | | MW | Distance | Neighbor |
|---|---|---|---|---|---|
| 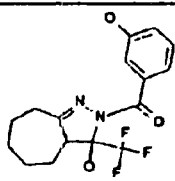 | BAS 3386059 | $C_{16}H_{17}F_3N_2O_3$ | 342.321 | 0.637 | Naloxone |
| 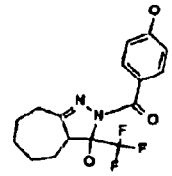 | BAS 1003176 | $C_{16}H_{17}F_3N_2O_3$ | 342.321 | 0.637 | Naloxone |
| 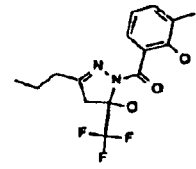 | BAS 1004848 | $C_{15}H_{17}F_3N_2O_3$ | 330.310 | 0.643 | Naloxone |
| 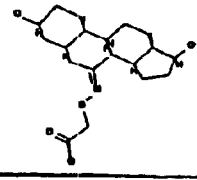 | MFCD00273259 | $C_{21}H_{33}NO_5$ | 379.501 | 0.644 | Nalmefene |
| 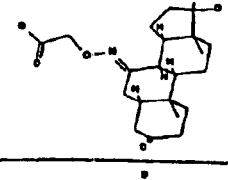 | MFCD00273270 | $C_{21}H_{31}NO_5$ | 377.485 | 0.646 | Naloxone |
| 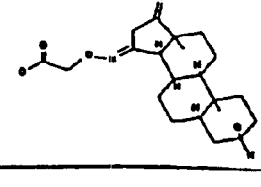 | MFCD00273266 | $C_{21}H_{31}NO_5$ | 377.485 | 0.648 | Naloxone |
| | | | | | |
Fig. 4C

200 Neighbors
| Structure | Cpd ID | | MW | Distance | Neighbor |
|---|---|---|---|---|---|
| 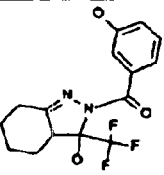 | BAS 3386023 | $C_{15}H_{15}F_3N_2O_3$ | 328.294 | 0.653 | Naloxone |
| 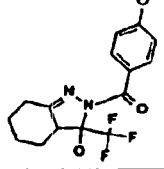 | BAS 2026128 | $C_{15}H_{15}F_3N_2O_3$ | 328.294 | 0.657 | Naloxone |
| 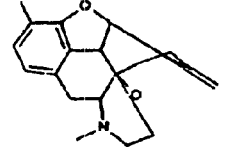 | 617005 | $C_{18}H_{21}NO_3$ | 299.373 | 0.658 | 6-beta-Naltrexol |
| 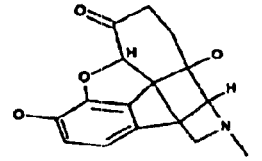 | MFCD00079194 | $C_{17}H_{19}NO_4$ | 301.345 | 0.662 | 6-beta-Naltrexol |
| 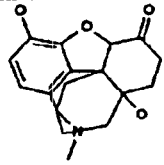 | 19045 | $C_{17}H_{19}NO_4$ | 301.345 | 0.666 | 6-beta-Naltrexol |
| 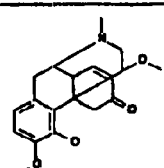 | 76021 | $C_{19}H_{23}NO_4$ | 329.399 | 0.673 | Nalmefene |
| | | | | | |
Fig. 4D

200 Neighbors

| Structure | Cpd ID | | MW | Distance | Neighbor |
|---|---|---|---|---|---|
| 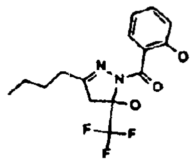 | BAS 1002442 | $C_{15}H_{17}F_3N_2O_3$ | 330.310 | 0.677 | Naloxone |
| 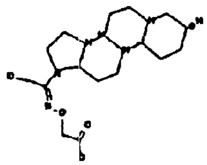 | MFCD00271723 | $C_{23}H_{37}NO_5$ | 407.555 | 0.682 | Naloxone |
| 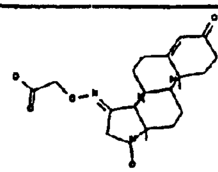 | MFCD00273273 | $C_{21}H_{29}NO_5$ | 375.469 | 0.688 | Nalmefene |
| 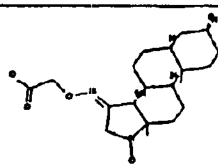 | MFCD00273264 | $C_{21}H_{33}NO_5$ | 379.501 | 0.697 | Nalmefene |
| 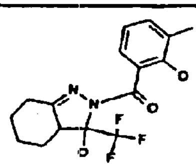 | BAS 2026145 | $C_{16}H_{17}F_3N_2O_3$ | 342.321 | 0.698 | Naloxone |
| 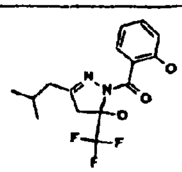 | BAS 3387114 | $C_{15}H_{17}F_3N_2O_3$ | 330.310 | 0.704 | Naloxone |
| | | | | | |

Fig. 4E

200 Neighbors
| Structure | Cpd ID | | MW | Distance | Neighbor |
|---|---|---|---|---|---|
| 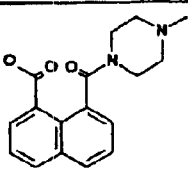 | 376679 | $C_{17}H_{18}N_2O_3$ | 298.345 | 0.705 | Naltrexone |
| 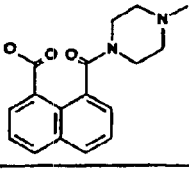 | 379963 | $C_{17}H_{18}N_2O_3$ | 298.345 | 0.705 | Naltrexone |
| 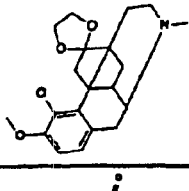 | 157870 | $C_{20}H_{27}NO_4$ | 345.442 | 0.714 | Nalmefene |
| 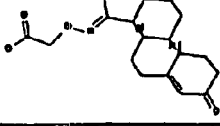 | MFCD00273274 | $C_{21}H_{27}NO_5$ | 373.453 | 0.720 | Naloxone |
| 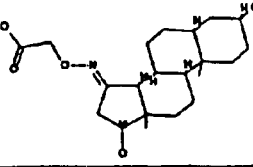 | MFCD00273260 | $C_{21}H_{33}NO_5$ | 379.501 | 0.723 | Nalmefene |
| 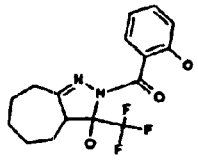 | BAS 1003163 | $C_{16}H_{17}F_3N_2O_3$ | 342.321 | 0.727 | Naloxone |
Fig. 4F

200 Neighbors
| Structure | Cpd ID | | MW | Distance | Neighbor |
|---|---|---|---|---|---|
| 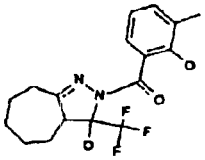 | BAS 1003182 | $C_{17}H_{19}F_3N_2O_3$ | 356.348 | 0.739 | Naltrexone |
| 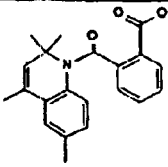 | BAS 0510629 | $C_{21}H_{21}NO_3$ | 335.406 | 0.756 | Naltrexone |
| 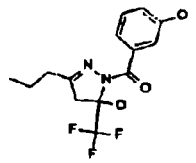 | BAS 1002419 | $C_{14}H_{15}F_3N_2O_3$ | 316.282 | 0.757 | Naloxone |
| 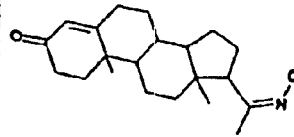 | 18579 | $C_{23}H_{33}NO_4$ | 387.524 | 0.760 | Nalmefene |
| 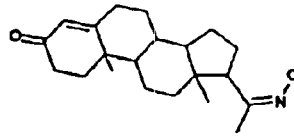 | 58796 | $C_{23}H_{33}NO_4$ | 387.524 | 0.760 | Nalmefene |
| 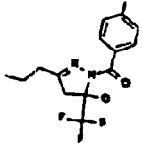 | BAS 1004835 | $C_{14}H_{15}F_3N_2O_3$ | 316.282 | 0.763 | Naloxone |
| | | | | | |
Fig. 4G

200 Neighbors
| Structure | Cpd ID | | MW | Distance | Neighbor |
|---|---|---|---|---|---|
| 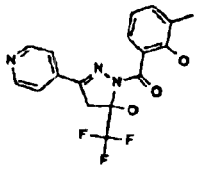 | BAS 2004373 | $C_{17}H_{14}F_3N_3O_3$ | 365.315 | 0.765 | Naloxone |
| 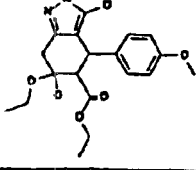 | 693856 | $C_{19}H_{24}N_2O_6$ | 376.413 | 0.768 | Nalmefene |
| 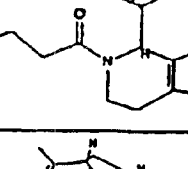 | MFCD01764789 | $C_{17}H_{17}F_3N_2O_3$ | 354.332 | 0.769 | Naloxone |
| 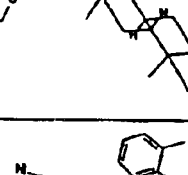 | MFCD00271738 | $C_{23}H_{37}NO_4$ | 391.556 | 0.772 | Nalmefene |
| 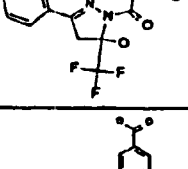 | BAS 2025996 | $C_{17}H_{14}F_3N_3O_3$ | 365.315 | 0.774 | Naloxone |
| 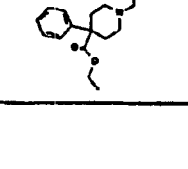 | BAS 2282169 | $C_{22}H_{25}NO_4$ | 367.449 | 0.780 | Nalmefene |
| | | | | | |
Fig. 4H

200 Neighbors
| Structure | Cpd ID | | MW | Distance | Neighbor |
|---|---|---|---|---|---|
| 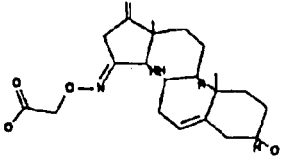 | MFCD00273268 | $C_{21}H_{29}NO_5$ | 375.469 | 0.789 | Naloxone |
| 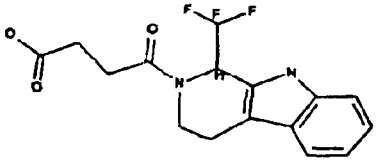 | MFCD00179880 | $C_{16}H_{15}F_3N_2O_3$ | 340.305 | 0.800 | Naloxone |
| 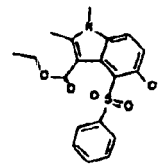 | BAS 1507170 | $C_{19}H_{19}NO_5S$ | 373.431 | 0.801 | Nalmefene |
| 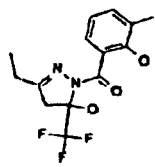 | BAS 3386088 | $C_{14}H_{15}F_3N_2O_3$ | 316.282 | 0.802 | Naloxon |
| 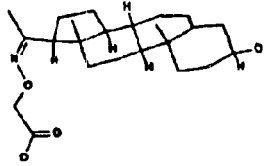 | MFCD00272082 | $C_{23}H_{35}NO_4$ | 389.540 | 0.818 | Nalmefene |
| 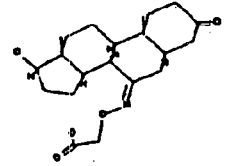 | MFCD00271113 | $C_{21}H_{31}NO_5$ | 377.485 | 0.829 | 6-beta-Naltrexol |
| | | | | | |
Fig. 4I

200 Neighbors

| Structure | Cpd ID | | MW | Distance | Neighbor |
|---|---|---|---|---|---|
| 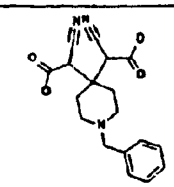 | 116054 | $C_{18}H_{19}N_3O_4$ | 341.370 | 0.831 | 6-beta-Naltrexol |
| 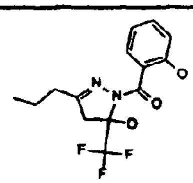 | BAS 1004837 | $C_{14}H_{15}F_3N_2O_3$ | 316.282 | 0.835 | Naloxone |
| 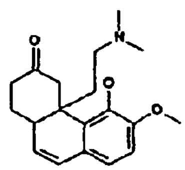 | 134536 | $C_{19}H_{25}NO_3$ | 315.416 | 0.838 | 6-beta-Naltrexol |
| 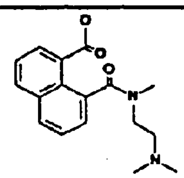 | 615801 | $C_{17}H_{20}N_2O_3$ | 300.361 | 0.856 | Naltrexone |
| 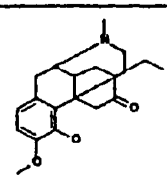 | 404374 | $C_{20}H_{27}NO_3$ | 329.443 | 0.870 | Nalmefene |
| 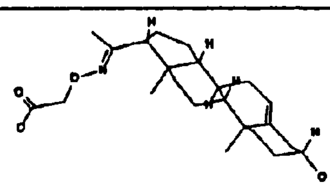 | MFCD00273318 | $C_{23}H_{35}NO_4$ | 389.540 | 0.870 | Nalmefene |

Fig. 4J

200 Neighbors

| Structure | Cpd ID | | MW | Distance | Neighbor |
|---|---|---|---|---|---|
| 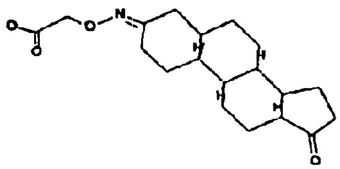 | MFCD00271094 | $C_{21}H_{31}NO_4$ | 361.486 | 0.877 | Nalmefene |
| 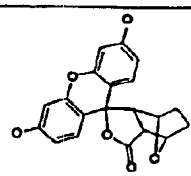 | 202587 | $C_{20}H_{16}O_6$ | 352.347 | 0.889 | Nalmefene |
| 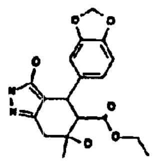 | 693862 | $C_{18}H_{20}N_2O_6$ | 360.370 | 0.892 | Nalmefene |
| 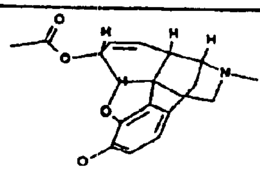 | MFCD00467140 | $C_{19}H_{21}NO_4$ | 327.384 | 0.905 | Nalmefene |
| 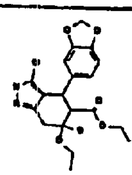 | 693863 | $C_{19}H_{22}N_2O_7$ | 390.396 | 0.909 | Naltrexone |
| 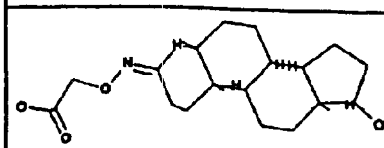 | MFCD00271196 | $C_{21}H_{33}NO_4$ | 363.501 | 0.912 | Nalmefene |
| | | | | | |

Fig. 4K

200 Neighbors

| Structure | Cpd ID | | MW | Distance | Neighbor |
|---|---|---|---|---|---|
| 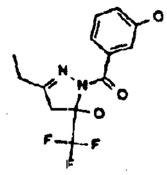 | BAS 3386092 | $C_{13}H_{13}F_3N_2O_3$ | 302.255 | 0.919 | Naloxone |
| 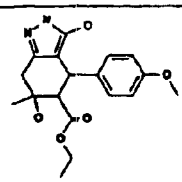 | 593855 | $C_{18}H_{22}N_2O_5$ | 346.386 | 0.923 | Nalmefene |
| 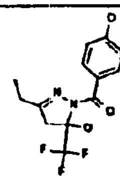 | BAS 3386091 | $C_{13}H_{13}F_3N_2O_3$ | 302.255 | 0.928 | Naloxone |
| 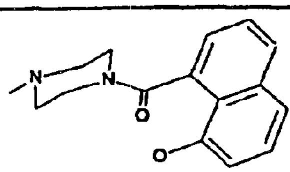 | MFCD00665833 | $C_{16}H_{18}N_2O_2$ | 270.334 | 0.929 | Naltrexone |
| 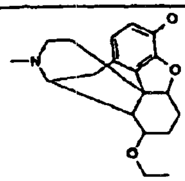 | 404368 | $C_{19}H_{25}NO_3$ | 315.416 | 0.941 | 6-beta-Naltrexol |
| 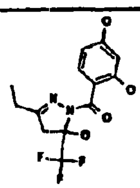 | BAS 0606820 | $C_{13}H_{13}F_3N_2O_4$ | 318.255 | 0.948 | Naloxone |
| | | | | | |

Fig. 4L

200 Neighbors
| Structure | Cpd ID | | MW | Distance | Neighbor |
|---|---|---|---|---|---|
| 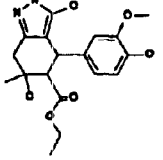 | 693859 | $C_{18}H_{22}N_2O_6$ | 362.388 | 0.949 | Nalmefene |
| 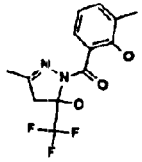 | BAS 0436353 | $C_{13}H_{13}F_3N_2O_3$ | 302.255 | 0.965 | Naloxone |
| 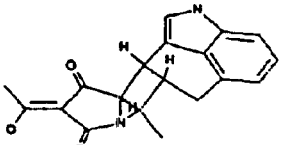 | MFCD00167445 | $C_{20}H_{20}N_2O_3$ | 336.394 | 0.968 | Naltrexone |
| 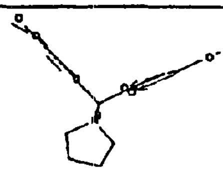 | MFCD00667402 | $C_{21}H_{25}NO_6$ | 387.437 | 0.974 | Nalmefene |
| 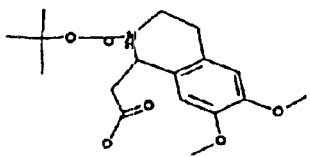 | MFCD02258126 | $C_{18}H_{25}NO_6$ | 351.403 | 0.977 | Naloxone |
| 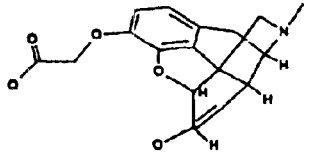 | MFCD00143186 | $C_{19}H_{21}NO_5$ | 343.383 | 0.985 | Naltrexone |
Fig. 4M

200 Neighbors

| Structure | Cpd ID | | MW | Distance | Neighbor |
|---|---|---|---|---|---|
| 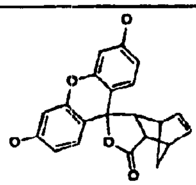 | 119887 | $C_{21}H_{16}O_5$ | 348.359 | 0.993 | Naloxone |
| 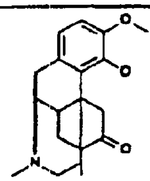 | 404365 | $C_{19}H_{25}NO_3$ | 315.416 | 1.002 | Nalmefene |
| 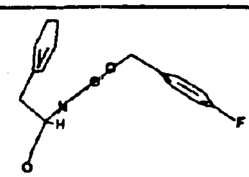 | MFCD01871411 | $C_{21}H_{20}FNO_3$ | 353.397 | 1.012 | Naloxone |
| 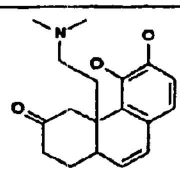 | 152720 | $C_{18}H_{23}NO_3$ | 301.389 | 1.015 | 6-beta-Naltrxol |
| 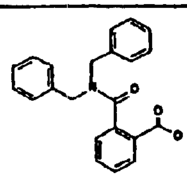 | 117581 | $C_{22}H_{19}NO_3$ | 345.402 | 1.016 | Naloxone |
| 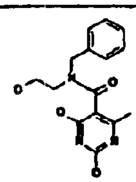 | 669466 | $C_{15}H_{17}N_3O_4$ | 303.320 | 1.017 | Naloxone |
| | | | | | |

Fig. 4N

200 Neighbors
| Structure | Cpd ID | | MW | Distance | Neighbor |
|---|---|---|---|---|---|
| 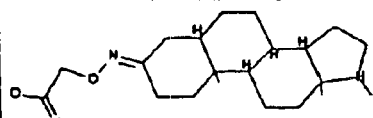 | MFCD00271129 | $C_{21}H_{33}NO_4$ | 363.501 | 1.029 | Nalmefene |
| 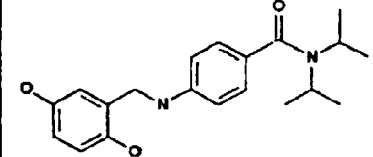 | 689431 | $C_{20}H_{26}N_2O_3$ | 342.442 | 1.035 | 6-beta-Naltrexol |
| 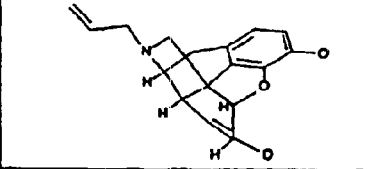 | MFCD00056772 | $C_{19}H_{21}NO_3$ | 311.384 | 1.039 | Nalmefene |
| 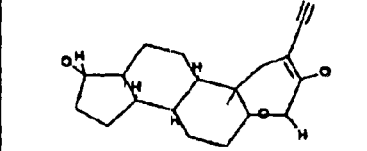 | MFCD00199295 | $C_{20}H_{27}NO_3$ | 329.443 | 1.045 | Nalmefene |
| 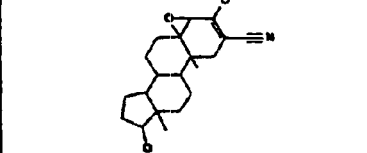 | R191489 | $C_{20}H_{27}NO_3$ | 329.443 | 1.046 | Nalmefene |
| 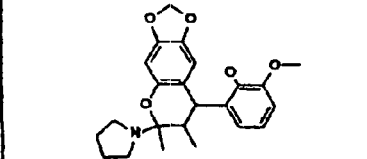 | 375504 | $C_{23}H_{27}NO_5$ | 397.475 | 1.050 | Naloxone |
| | | | | | |
Fig. 40

200 Neighbors

| Structure | Cpd ID | | MW | Distance | Neighbor |
|---|---|---|---|---|---|
| 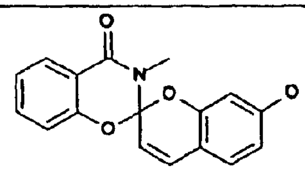 | 692397 | $C_{17}H_{13}NO_4$ | 295.297 | 1.068 | Naloxone |
| 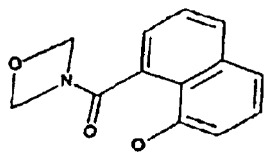 | MFCD00433684 | $C_{15}H_{15}NO_3$ | 257.292 | 1.069 | Naloxone |
| 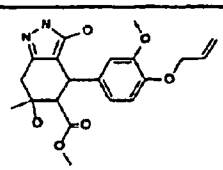 | 693860 | $C_{20}H_{24}N_2O_6$ | 388.424 | 1.071 | Nalmefene |
| 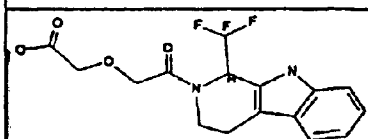 | MFCD01764791 | $C_{16}H_{15}F_3N_2O_4$ | 356.304 | 1.073 | Naloxone |
| 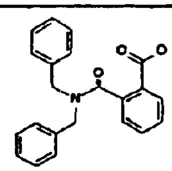 | BAS 1519270 | $C_{22}H_{19}NO_3$ | 345.402 | 1.078 | Naloxone |
| 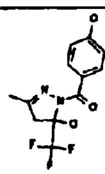 | BAS 3385849 | $C_{12}H_{11}F_3N_2O_3$ | 288.228 | 1.083 | Naloxone |
| | | | | | |

Fig. 4P

200 Neighbors

| Structure | Cpd ID | | MW | Distance | Neighbor |
|---|---|---|---|---|---|
| 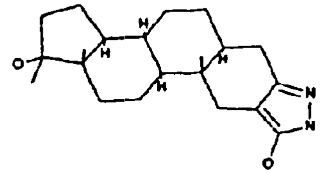 | MFCD00673308 | $C_{21}H_{32}N_2O_2$ | 344.501 | 1.087 | Nalmefene |
| 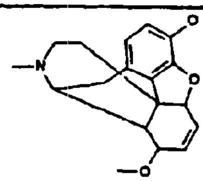 | 404356 | $C_{18}H_{21}NO_3$ | 299.373 | 1.099 | Nalmefene |
| 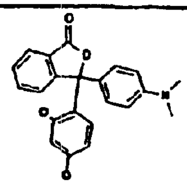 | 43938 | $C_{22}H_{19}NO_4$ | 361.401 | 1.107 | Nalmefene |
| 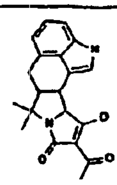 | 117181 | $C_{20}H_{20}N_2O_3$ | 336.394 | 1.109 | Naltrexone |
| 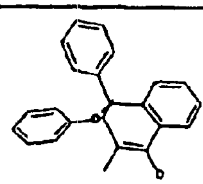 | MFCD00094379 | $C_{24}H_{22}O_2$ | 342.442 | 1.111 | Nalmefene |
| 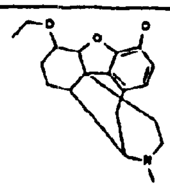 | 404369 | $C_{19}H_{25}NO_3$ | 315.418 | 1.111 | 6-beta-Naltrexol |
| | | | | | |

Fig. 4Q

200 Neighbors

| Structure | Cpd ID |  | MW | Distance | Neighbor |
|---|---|---|---|---|---|
| 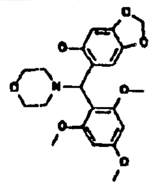 | 381577 | $C_{21}H_{25}NO_7$ | 403.436 | 1.111 | Naloxone |
| 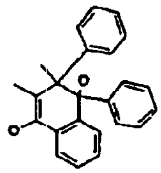 | S842214 | $C_{24}H_{22}O_2$ | 342.442 | 1.112 | Nalmefene |
| 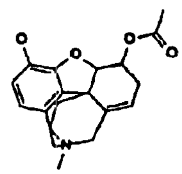 | 134602 | $C_{19}H_{21}NO_4$ | 327.384 | 1.112 | 6-beta-Naltrexol |
| 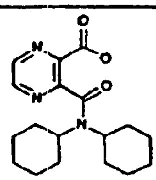 | CHS 0316796 | $C_{18}H_{25}N_3O_3$ | 331.418 | 1.113 | Naloxone |
| 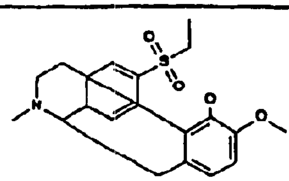 | 134604 | $C_{20}H_{25}NO_4S$ | 375.491 | 1.115 | Nalmefene |
| 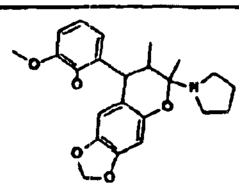 | R171697 | $C_{23}H_{27}NO_5$ | 397.475 | 1.133 | Nalmefene |

Fig. 4R

200 Neighbors

| Structure | Cpd ID | | MW | Distance | Neighbor |
|---|---|---|---|---|---|
| 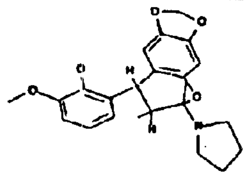 | MFCD00667401 | $C_{23}H_{27}NO_5$ | 397.475 | 1.134 | Nalmefene |
| 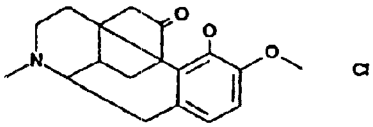 | S959863 | $C_{18}H_{24}ClNO_3$ | 337.850 | 1.137 | 6-beta-Naltrexol |
| 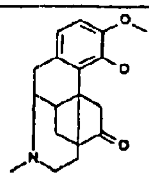 | 35545 | $C_{18}H_{23}NO_3$ | 301.389 | 1.137 | 6-beta-Naltrexol |
| 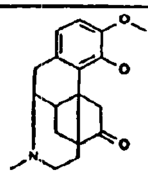 | 134598 | $C_{18}H_{23}NO_3$ | 301.389 | 1.137 | 6-beta-Naltrexol |
| 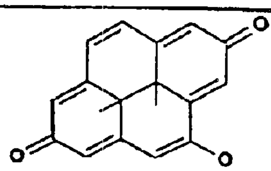 | S310778 | $C_{18}H_{14}O_3$ | 278.310 | 1.140 | Naloxone |
| 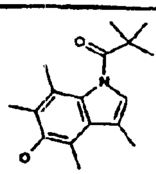 | 669800 | $C_{17}H_{23}NO_2$ | 273.378 | 1.141 | Naloxone |
| | | | | | |

Fig. 4S

200 Neighbors
| Structure | Cpd ID | | MW | Distance | Neighbor |
|---|---|---|---|---|---|
| 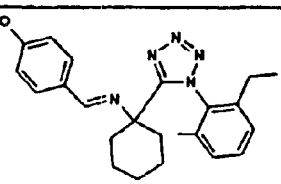 | BAS 0083962 | $C_{23}H_{27}N_5O$ | 389.505 | 1.141 | Naltrexone |
| 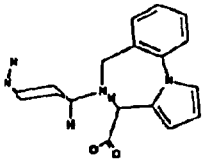 | MFCD01765597 | $C_{18}H_{21}N_3O_2$ | 311.387 | 1.142 | 6-beta-Naltrexol |
| 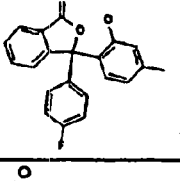 | 682334 | $C_{21}H_{15}FO_3$ | 334.350 | 1.143 | Naloxone |
| 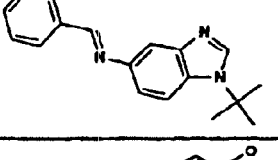 | BAS 0631739 | $C_{18}H_{19}N_3O$ | 293.372 | 1.143 | Nalmefene |
| 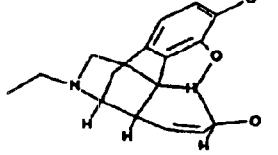 | MFCD00144882 | $C_{18}H_{21}NO_3$ | 299.373 | 1.149 | 6-beta-Naltrexol |
| 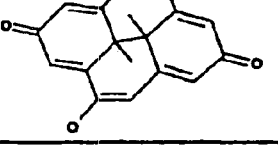 | MFCD00229975 | $C_{18}H_{14}O_3$ | 278.310 | 1.150 | Naloxone |
Fig. 4T

200 Neighbors
| Structure | Cpd ID | | MW | Distance | Neighbor |
|---|---|---|---|---|---|
| 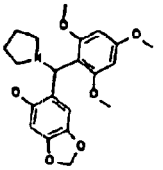 | R171700 | $C_{21}H_{25}NO_6$ | 387.437 | 1.157 | Nalmefene |
| 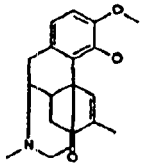 | 134592 | $C_{19}H_{23}NO_3$ | 313.400 | 1.163 | 6-beta-Naltrexol |
| 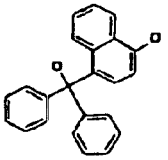 | 401210 | $C_{23}H_{18}O_2$ | 326.399 | 1.166 | Nalmefene |
| 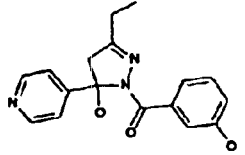 | BAS 2026074 | $C_{17}H_{17}N_3O_3$ | 311.343 | 1.172 | Naltrexone |
| 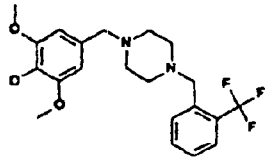 | BAS 3050727 | $C_{21}H_{25}F_3N_2O_3$ | 410.440 | 1.177 | Nalmefene |
| 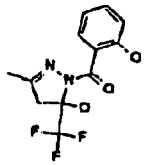 | BAS 0341630 | $C_{12}H_{11}F_3N_2O_3$ | 288.228 | 1.185 | Naloxone |
| | | | | | |
Fig. 4U

200 Neighbors

| Structure | Cpd ID | | MW | Distance | Neighbor |
|---|---|---|---|---|---|
| 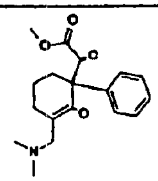 | 97817 | $C_{18}H_{23}NO_4$ | 317.388 | 1.190 | Naloxone |
| 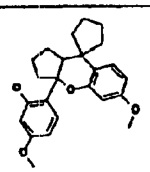 | ASN 3185453 | $C_{24}H_{28}O_4$ | 380.488 | 1.196 | Naloxone |
| 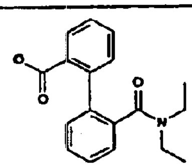 | 21257 | $C_{18}H_{19}NO_3$ | 297.357 | 1.196 | 6-beta-Naltrexol |
| 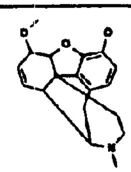 | 134601 | $C_{18}H_{21}NO_3$ | 299.373 | 1.200 | 6-beta-Naltrexol |
| | BAS 2026075 | $C_{17}H_{17}N_3O_3$ | 311.343 | 1.203 | 6-beta-Naltrexol |
| | BAS 1996620 | $C_{16}H_{15}N_3O_3$ | 297.316 | 1.211 | 6-beta-Naltrexol |

Fig. 4V

200 Neighbors

| Structure | Cpd ID | | MW | Distance | Neighbor |
|---|---|---|---|---|---|
| 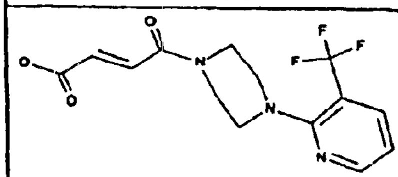 | MFCD01314356 | $C_{14}H_{14}F_3N_3O_3$ | 329.281 | 1.215 | Naloxone |
| 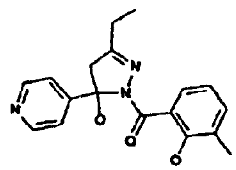 | BAS 2026097 | $C_{18}H_{19}N_3O_3$ | 325.370 | 1.221 | Naltrexone |
| | BAS 1914007 | $C_{21}H_{30}N_2O_3$ | 358.485 | 1.221 | Naloxone |
| 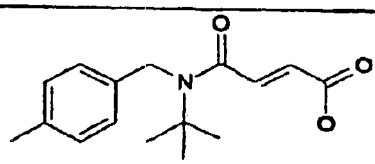 | CHS 0003221 | $C_{16}H_{21}NO_3$ | 275.351 | 1.227 | Naloxone |
| 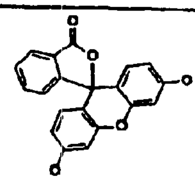 | 667256 | $C_{20}H_{12}O_5$ | 332.318 | 1.227 | Naloxone |
| 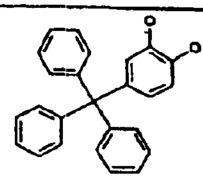 | 37625 | $C_{25}H_{20}O_2$ | 352.437 | 1.235 | Nalmefene |

Fig. 4W

200 Neighbors

| Structure | Cpd ID | | MW | Distance | Neighbor |
|---|---|---|---|---|---|
| 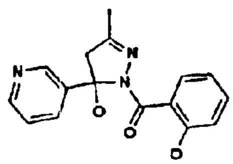 | BAS 1003093 | $C_{16}H_{15}N_3O_3$ | 297.316 | 1.236 | 6-beta-Naltrexol |
| 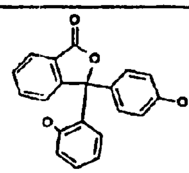 | 16468 | $C_{20}H_{14}O_4$ | 318.332 | 1.238 | Naloxone |
| 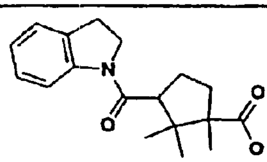 | CHS 0227049 | $C_{18}H_{23}NO_3$ | 301.389 | 1.241 | Naloxone |
| 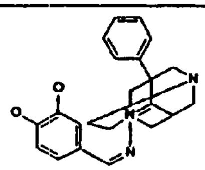 | BAS 0315050 | $C_{22}H_{24}N_4O_2$ | 376.462 | 1.241 | Nalmefene |
| 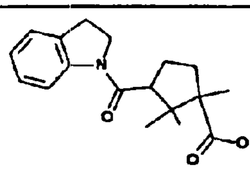 | BAS 1289763 | $C_{18}H_{23}NO_3$ | 301.389 | 1.242 | Naloxone |
| 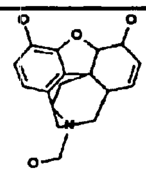 | 349127 | $C_{17}H_{19}NO_4$ | 301.345 | 1.243 | Naloxone |

Fig. 4X

200 Neighbors

| Structure | Cpd ID | | MW | Distance | Neighbor |
|---|---|---|---|---|---|
| 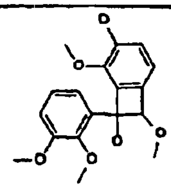 | 635928 | $C_{18}H_{20}O_6$ | 332.356 | 1.250 | Nalmefene |
| 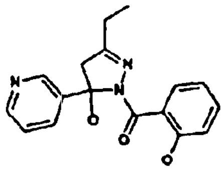 | BAS 2377555 | $C_{17}H_{17}N_3O_3$ | 311.343 | 1.251 | 6-beta-Naltrexol |
| 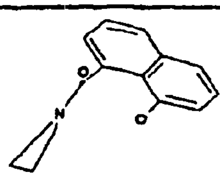 | MFCD00665835 | $C_{15}H_{15}NO_2$ | 241.292 | 1.251 | Naltrexone |
| 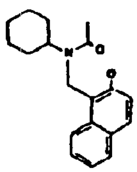 | 47931 | $C_{19}H_{23}NO_2$ | 297.401 | 1.255 | 6-beta-Naltrexol |
| 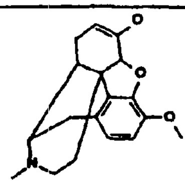 | 76435 | $C_{18}H_{21}NO_3$ | 299.373 | 1.257 | Nalmefene |
| 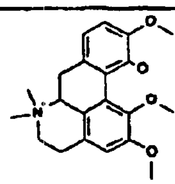 | 90558 | $C_{21}H_{26}NO_4$ | 356.446 | 1.258 | Naloxone |
| | | | | | |

Fig. 4Y

200 Neighbors

| Structure | Cpd ID | | MW | Distance | Neighbor |
|---|---|---|---|---|---|
| 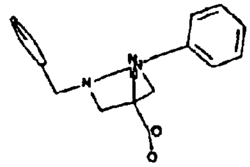 | MFCD00206273 | $C_{20}H_{21}N_3O_2$ | 335.409 | 1.261 | Naloxone |
| 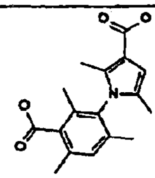 | 159208 | $C_{17}H_{19}NO_4$ | 301.345 | 1.267 | Nalmefene |
| 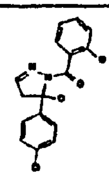 | BAS 0341580 | $C_{16}H_{13}ClN_2O_3$ | 316.747 | 1.267 | Naltrexone |
| 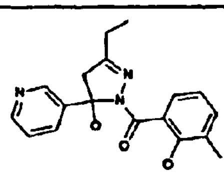 | BAS 2377575 | $C_{18}H_{19}N_3O_3$ | 325.370 | 1.268 | Naltrexone |
| 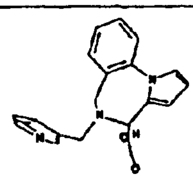 | MFCD01765638 | $C_{19}H_{17}N_3O_2$ | 319.366 | 1.268 | Nalmefene |
| 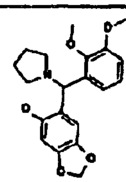 | R171484 | $C_{20}H_{23}NO_5$ | 357.410 | 1.268 | Nalmefene |
| | | | | | |

Fig. 4Z

200 Neighbors
| Structure | Cpd ID | | MW | Distance | Neighbor |
|---|---|---|---|---|---|
| 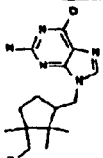 | 700350 | $C_{15}H_{23}N_5O_2$ | 305.383 | 1.272 | Naloxone |
| 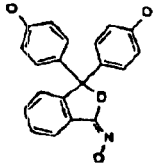 | 16907 | $C_{20}H_{15}NO_4$ | 333.347 | 1.274 | Nalmefene |
| 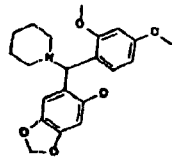 | R170623 | $C_{21}H_{25}NO_5$ | 371.437 | 1.275 | Nalmefene |
| 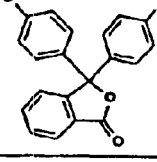 | S98907 | $C_{20}H_{14}O_4$ | 318.332 | 1.278 | Naloxone |
| 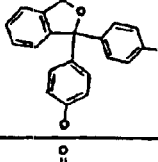 | 10464 | $C_{20}H_{14}O_4$ | 318.332 | 1.278 | Naloxone |
| 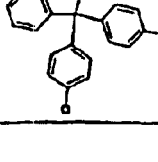 | 215214 | $C_{20}H_{14}O_4$ | 318.332 | 1.278 | Naloxone |
| | | | | | |
Fig. 4AA

200 Neighbors
| Structure | Cpd ID | | MW | Distance | Neighbor |
|---|---|---|---|---|---|
| 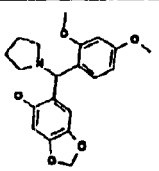 | R171425 | $C_{20}H_{23}NO_5$ | 357.410 | 1.280 | Nalmefene |
| 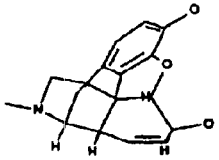 | MFCD00153032 | $C_{17}H_{19}NO_3$ | 285.346 | 1.283 | 6-beta-Naltrexol |
| 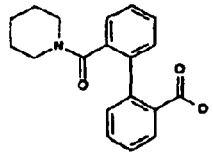 | S196991 | $C_{19}H_{19}NO_3$ | 309.368 | 1.285 | Naltrexone |
| 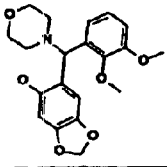 | R170291 | $C_{20}H_{23}NO_8$ | 373.409 | 1.286 | Naloxone |
| 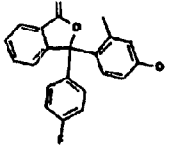 | 682335 | $C_{21}H_{15}FO_3$ | 334.350 | 1.287 | Naloxone |
| 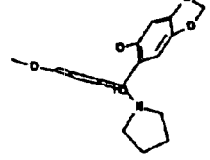 | MFCD00667377 | $C_{20}H_{23}NO_5$ | 357.410 | 1.289 | Nalmefene |
Fig. 4AB

200 Neighbors

| Structure | Cpd ID | | MW | Distance | Neighbor |
|---|---|---|---|---|---|
| 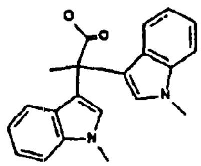 | 106242 | $C_{21}H_{20}N_2O_2$ | 332.408 | 1.294 | Naloxone |
| 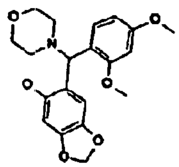 | R170410 | $C_{20}H_{23}NO_6$ | 373.409 | 1.299 | Naloxone |
| | MFCD00005912 | $C_{22}H_{18}O_4$ | 346.386 | 1.300 | Naloxone |
| 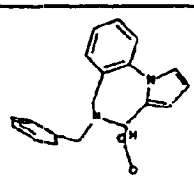 | MFCD01765837 | $C_{20}H_{18}N_2O_2$ | 318.379 | 1.302 | Nalmefene |
| 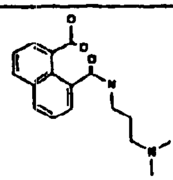 | 376678 | $C_{17}H_{20}N_2O_3$ | 300.361 | 1.303 | Naltrexone |
| 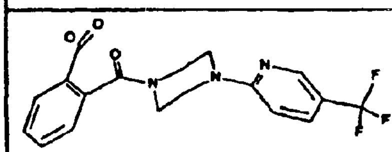 | MFCD01314431 | $C_{18}H_{16}F_3N_3O_3$ | 379.342 | 1.303 | Naloxone |
| | | | | | |

Fig. 4AC

200 Neighbors
| Structure | Cpd ID | | MW | Distance | Neighbor |
|---|---|---|---|---|---|
| 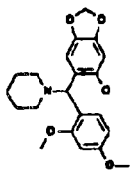 | 370278 | $C_{21}H_{25}NO_5$ | 371.437 | 1.304 | Nalmefene |
| 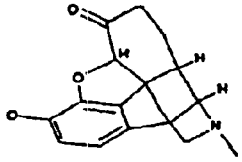 | MFCD00242635 | $C_{17}H_{19}NO_3$ | 285.346 | 1.305 | 6-beta-Naltrexol |
| 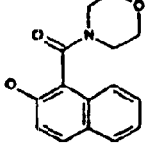 | S602965 | $C_{15}H_{15}NO_3$ | 257.292 | 1.306 | Naltrexone |
| 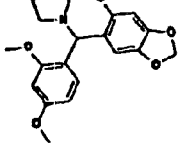 | 370279 | $C_{20}H_{23}NO_5$ | 357.410 | 1.306 | Nalmefene |
| 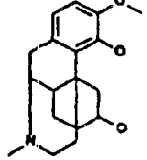 | 157877 | $C_{18}H_{25}NO_3$ | 303.405 | 1.310 | Nalmefene |
| 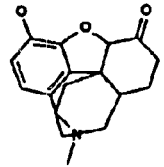 | 19046 | $C_{17}H_{19}NO_3$ | 285.346 | 1.310 | 6-beta-Naltrexol |
Fig. 4AD

200 Neighbors

| Structure | Cpd ID | | MW | Distance | Neighbor |
|---|---|---|---|---|---|
| 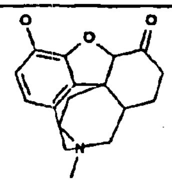 | 117862 | $C_{17}H_{19}NO_3$ | 285.348 | 1.310 | 6-beta-Naltrexol |
| 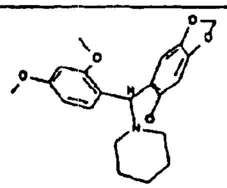 | MFCD00667305 | $C_{21}H_{25}NO_5$ | 371.437 | 1.313 | Nalmefene |
| 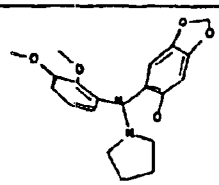 | MFCD00667382 | $C_{20}H_{23}NO_5$ | 357.410 | 1.316 | Nalmefene |
| 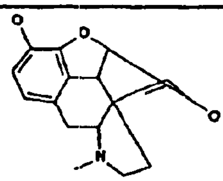 | 611276 | $C_{17}H_{19}NO_3$ | 285.346 | 1.318 | 6-beta-Naltrexol |
| 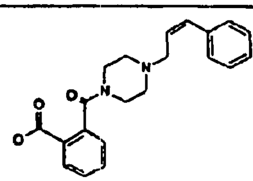 | BAS 1099232 | $C_{21}H_{22}N_2O_3$ | 350.421 | 1.320 | Naltrexone |
| 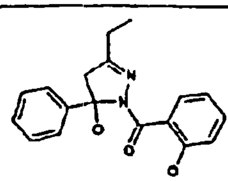 | BAS 0313319 | $C_{18}H_{18}N_2O_3$ | 310.356 | 1.321 | 6-beta-Naltrexol |
| | | | | | |

Fig. 4AE

200 Neighbors
| Structure | Cpd ID | | MW | Distance | Neighbor |
|---|---|---|---|---|---|
| 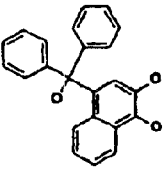 | 401211 | $C_{23}H_{18}O_3$ | 342.398 | 1.325 | Nalmefene |
| 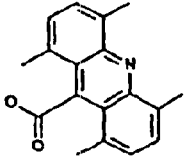 | 409635 | $C_{18}H_{17}NO_2$ | 279.342 | 1.326 | Nalmefene |
| 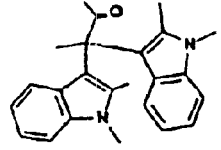 | 106231 | $C_{23}H_{24}N_2O_2$ | 360.460 | 1.327 | Naloxone |
| 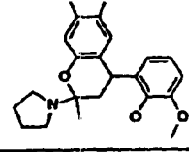 | 375505 | $C_{22}H_{25}NO_5$ | 383.448 | 1.329 | Naloxone |
| 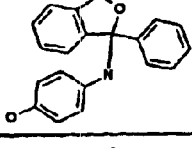 | BAS 1053035 | $C_{20}H_{15}NO_3$ | 317.347 | 1.331 | Naloxone |
| 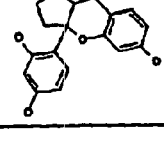 | ASN 3160807 | $C_{22}H_{24}O_4$ | 352.434 | 1.332 | Naloxone |
| | | | | | |
Fig. 4AF

200 Neighbors

| Structure | Cpd ID | | MW | Distance | Neighbor |
|---|---|---|---|---|---|
| 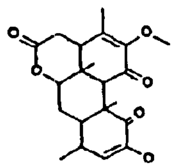 | 324633 | $C_{21}H_{26}O_6$ | 374.438 | 1.333 | Naloxone |
| 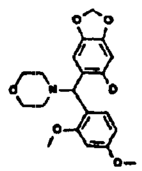 | 370277 | $C_{20}H_{23}NO_6$ | 373.409 | 1.339 | Naloxone |
| 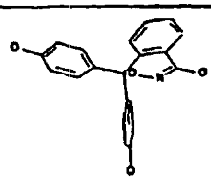 | MFCD00375811 | $C_{20}H_{15}NO_4$ | 333.347 | 1.343 | 6-beta-Naltrexol |
| 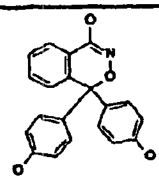 | BAS 0659522 | $C_{20}H_{15}NO_4$ | 333.347 | 1.343 | 6-beta-Naltrexol |
| 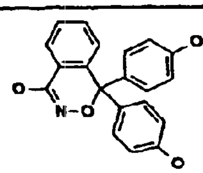 | CHS 0305736 | $C_{20}H_{15}NO_4$ | 333.347 | 1.343 | 6-beta-Naltrexol |
| 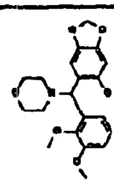 | 381576 | $C_{20}H_{23}NO_6$ | 373.409 | 1.346 | Naloxone |
| | | | | | |

Fig. 4AG

200 Neighbors
| Structure | Cpd ID | | MW | Distance | Neighbor |
|---|---|---|---|---|---|
| 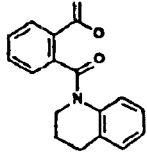 | CHS 0120289 | $C_{17}H_{15}NO_3$ | 281.314 | 1.348 | Naloxone |
| 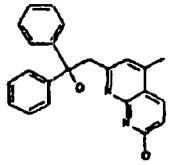 | 351159 | $C_{23}H_{20}N_2O_2$ | 356.428 | 1.349 | Nalmefene |
Fig. 4AH

INHIBITORS OF ABC DRUG TRANSPORTERS AT THE BLOOD-BRAIN BARRIER

CROSS-REFERENCE TO RELATED APPLICATIONS

This application claims priority of the following U.S. Patent Application Nos. 60/244,482, filed Oct. 30, 2000 (provisional); 60/245,110, filed Nov. 1, 2000 (provisional); and 60/246,235, filed Nov. 2, 2000 (provisional). The applications cited above are hereby incorporated herein by reference in their entirety to provide continuity of disclosure.

INTRODUCTION

Background

ATP-binding cassette (ABC) proteins play a central role in living cells through their role in nutrient uptake, protein, drug and antibiotic secretion, osmoregulation, antigen presentation, signal transduction and others. The majority of ABC proteins have a translocation function either in import of substrates or secretion of cellular products or xenobiotics.

The ATP-binding cassette (ABC) superfamily is one of the largest superfamilies known. With the multiplication of genome sequencing projects, new sequences appear every week in the GenBank database. Members of this family posses a highly conserved protein or module, the ABC module, that displays the WalkerA and WalkerB motifs separated by a short, highly conserved, sequence (consensus LSGGQ) called a signature sequence or linker peptide. Most ABC cassette proteins are primary transporters for unidirectional movement of molecules across biological membranes. The substrates handled by these transporters are extraordinarily varied ranging from small molecules to macromolecules.

ABC proteins of particular interest are the drug transporters associated with multidrug resistance in humans. The structure and function of drug transporters have been extensively reviewed, including by Benet, et al., J. Control. Rel. 39:139–143 (1996) for the gut barrier, by Chiou, et al., Pharm. Res. 17(8):903–905 (2000) for the liver barrier (and includes gut barrier references), and by Tduji, et al., in Adv. Drug Deliv. Rev. 36:277–290 (1999) for the blood-brain barrier. The family of drug transporters includes two different subfamilies, the multidrug resistance (MDR) proteins, such as PGP, and the multidrug resistance-associate protein (MRP) family. The human multidrug resistance-associated protein family currently has seven members (Borst et al, J. Natl Cancer Inst. 92:1295-(2000)). See also, Barrand, et al, Gen. Pharmacol. 28:639–645 (1997).

Originally implicated in the resistance of tumor cells to chemotherapeutic agents, the multi-drug resistance protein MDR1, also known as P-glycoprotein (PGP), belongs to the ATP-binding cassette family of proteins. See, e.g., Schinkel, Adv. Drug Deliv. Rev. 36:179–194 (1999). P-glycoprotein is an ATP-dependent drug transporter that is predominantly found in the apical membranes of a number of epithelial cell types in the body, including the luminal membrane of the brain capillary endothelial cells that make up the blood-brain barrier. Expression of PGP, localized to cell membranes may affect the bioavailability of drug molecules that are substrates for this transporter. Knockout mice lacking the gene encoding P-glycoprotein show elevated brain concentrations of multiple systemically administered drugs, including opioids as wells as chemotherapeutic agents. Chen and Pollack, J. Pharm. Exp. Ther. 287:545–552 (1998) and Thompson, et al., Anesthesiology 92:1392–1299 (2000).

Differences exist between the MRP and P-glycoprotein transporters. For example, resistance modulators useful against P-glycoprotein are less effective in reversing MRP-mediated resistance. It is not fully understood how MRP brings about drug efflux, but it is clear that the underlying mechanisms are different from those responsible for P-glycoprotein mediated drug efflux. In particular, glutathione (GSH) is required for the effective expulsion of anticancer agents via MRP transporting. Unlike P-glycoprotein, MRP is able to transport metallic oxyanions and glutathione and other conjugates, including peptidyl leukotrienes. Agents that inhibit organic ion transport, such as probenecid, can block MRP activity.

The blood brain barrier is a capillary barrier comprising a continuous layer of tightly bound endothelial cells. The interendothelial junctions between the cells of the blood brain barrier act to keep potentially noxious substances away from the brain. The continuity produced by the tight junctions between individual cells of the blood brain barrier enables the cerebrocapillary endothelium to act like a plasma membrane. Small molecules (m.w.<200 daltons) having a high degree of lipid solubility and low ionization at physiological pH are freely passed through the blood brain barrier. However, larger substances are substantially excluded. This protects the brain microenvironment from rapid changes in the composition of the blood.

Numerous pharmaceutical substances have their pharmacological action in the central nervous system. However, delivering these pharmaceutical substances to their active sites in the central nervous system (CNS), particularly the brain, can be problematic due to the very limited permeability of the blood brain barrier, which discourages transport of many therapeutically active agents into the brain. Additionally, the blood brain barrier may actively export molecules that cross the barrier, e.g., by leakage through the tight junctions between the endothelial cells or by non-specific passive diffusion across the endothelial membrane. After the compounds enter the brain, active efflux of these compound from the apical surface of the endothelial cells would place the compounds back into the endothelial cells and thus back into the blood. Such a mechanism would effectively decrease the cerebral concentration of these compounds.

One important class of CNS-active agents is the class of opioid compounds. Opioid receptor agonists, including morphine sulfate (hereafter called morphine or MS), have been marketed for many years and are widely used for the relief of moderate to severe acute and chronic pain. An opioid receptor agonist, such as morphine, exerts its primary effects on the central nervous system and organs containing smooth muscle, and acts as an agonist interacting with stereospecific and saturable binding sites or receptors in the brain, spinal cord, and other tissues. The principal therapeutic actions are analgesia and sedation.

Opioid receptor antagonists are generally accepted for use in the treatment of human conditions of ailments for reversing opioid toxicity and overdoses, and in preventing abuse of opioid receptor agonists, such as heroin or morphine. For these uses, the antagonists such as naloxone or naltrexone is used in relatively high concentrations in order to effectively block the activity and/or effects of the opioid receptor agonist by antagonizing the opioid receptor agonist at opioid receptors on nociceptive neurons.

The ability of the blood brain barrier to protect the nervous system from exogenous substances has impeded the development of therapies for a wide variety of disorders and conditions of the central nervous system. Thus, a continuing need exists for methods to increase the ability of clinicians administer bioactive substances across the blood brain barrier. The blood brain barrier presents a particularly difficult obstacle to treating conditions in which the therapeutic agents must act upon sites within the central nervous system, particularly the brain.

SUMMARY OF THE INVENTION

The present invention is directed to novel methods and compositions with drug transporter inhibitors. Such inhibitors according to the invention modulate the activity of ABC transporter proteins and include inhibitors of MDR proteins, such as PGP, as well as MRP proteins. Such methods and compositions are designed to achieve, for example, enhanced efficacy of opioid and/or non-opioid CNS-active agents, prevention and/or reversal of tolerance to, dependence upon or withdrawal from opioid and/or non-opioid CNS-active agents, as well as improved treatment of chronic pain patients.

The present invention is based in part on surprising results from transport studies of drug agents across the blood brain barrier that demonstrate that compounds of a defined structure according to the invention, including naltrexone, nalmafene and naloxone, are inhibitors of ABC transporter proteins, such as PGP, and unexpectedly increase the concentration in the brain of CNS-active agents, including opioid receptor agonists such as morphine and oxycodone. Also unexpectedly demonstrated is the reduction of efflux of such CNS-active agents from the brain by inhibitors of ABC transporter proteins according to the invention. The present invention provides a novel class of drug transporter inhibitors that act by inhibiting ABC transporter proteins and further provides a pharmacophore that allows the identification of new drug targets that are inhibitors of ABC transporter proteins. Also provided are new methods of screening for and/or identifying compounds that inhibit the transport (e.g., efflux or influx) of CNS-active agents across the blood brain barrier. Further provided are new methods of screening for and/or identifying CNS-active agents that are substrates for ABC transporter proteins. ABC transporter inhibitors identified according to the invention increase brain concentrations of CNS-active agents. Such inhibitors increase the influx into the brain and/or or reduce the efflux from the brain of such CNS-active agents.

The present invention provides methods and compositions for enhancing the efficacy of a non-opioid CNS-active agent by co-administering to a patient a therapeutic or sub-therapeutic dose of the non-opioid CNS-active agent and an amount of an inhibitor of a drug transporter effective to reduce efflux of the non-opioid CNS-active agent from the brain and/or to increase the concentration of the non-opioid CNS-active agent in the brain, where the drug transporter is an ABC drug transporter.

The present invention also methods and compositions for enhancing the efficacy of an opioid CNS-active agent by co-administering a therapeutic or sub-therapeutic dose of the opioid CNS-active agent with a non-opioid drug transporter inhibitor, such that the amount of non-opioid drug transporter inhibitor is effective to reduce efflux of the opioid CNS-active agent from the brain and/or to increase the concentration of the opioid CNS-active agent in the brain.

The present invention further provides methods and compositions for reversing or preventing tolerance to CNS-active agent, including an opioid CNS-active agent, by administering a drug transporter inhibitor to a patient, including a patient who is tolerant to the CNS-active agent, such that the amount of drug transporter inhibitor administered is sufficient to decrease efflux of the CNS-active agent form the brain and/or to increase the concentration of the CNS-active agent in the brain.

The present invention also provides methods of treating a patient experiencing chronic pain by co-administering to a patient a therapeutic or sub-therapeutic dose of an CNS-active agent, including an opioid CNS-active agent, and an amount of a drug transporter inhibitor effective to increase the concentration of the CNS-active agent in the brain. The co-administration may be repeated over a period of time that is greater than the period of time in which the patient would develop tolerance to or develop a dependence upon the CNS-active agent administered in the absence of the drug transporter inhibitor.

The invention also provides methods of controlling chronic pain without tolerance, dependence and/or withdrawal by co-administering a therapeutic or sub-therapeutic dose of a CNS-active agent, including an opioid CNS-active agent, and an amount of a drug transporter inhibitor effective to decrease efflux of the CNS-active agent form the brain and/or increase the concentration of CNS-active agent, including an opioid CNS-active agent, in the brain.

The present invention further provides methods and composition for enhancing the efficacy of a non-opioid CNS-active agent by co-administering non-opioid CNS-active agent with an opioid receptor antagonist, such that the amount of antagonist is effective to reduce efflux of the agent from the brain and/or increase the concentration of the agent in the brain.

BRIEF DESCRIPTION OF THE DRAWINGS

FIG. 1 illustrates the chemical structures of naltrexone, naloxone, nalmefene, 6-β-naltrexol and nalorphine.

FIGS. 4A–HH provide the 200 nearest neighbors of opioid analogues examined in the QSAR analysis.

DETAILED DESCRIPTION

Figure 2:
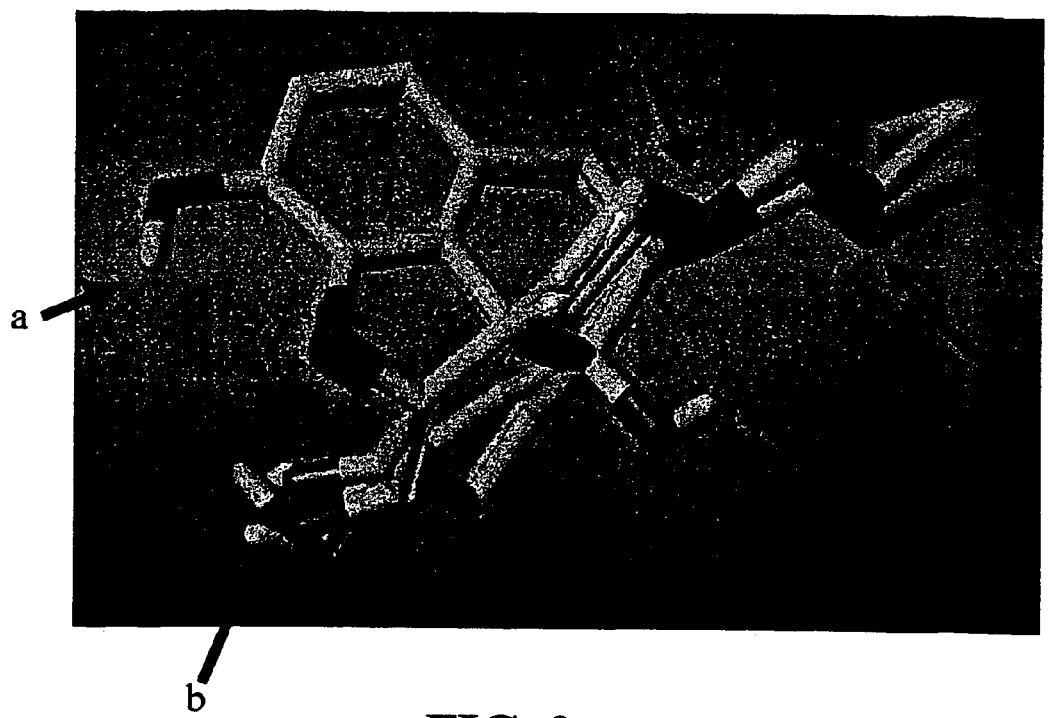
FIG. 2 presents an overlay of the opioid analogues, naltrexone, naloxone, nalmefene, 6-β-naltrexol and nalorphine.

The present invention is based in part on surprising results from transport studies of drug agents across the blood brain barrier that demonstrates that compounds previously identified as opioid receptor antagonists are inhibitors of ABC drug transporter proteins, including of the P-glycoprotein found at the blood brain barrier, PGP1a. Administration of opioid receptor antagonists, such as naloxone, nalmefene and naltrexone, unexpectedly resulted in increased brain concentrations of co-administered therapeutic agents, such as CNS-active agents. Such antagonists also unexpectedly reduced the efflux and/or increased the influx of the co-administered agents. The present invention provides a novel class of drug transporter inhibitors that act by inhibiting ABC transporter proteins and their associated ATPase as described herein and further provides a pharmacophore that identifies new drug targets that are inhibitors of ABC transporter proteins. As used herein, the terms "transporter" and "drug transporter" refer to a protein for the carrier-mediated influx and efflux of drugs and endocytosis of biologically active molecules, including across a gut, liver, or blood-brain barrier. An inhibitor of a transporter is expected to increase the bioavailability of an active agent according to the invention, wherein the transporter inhibitor reduces efflux across the blood-brain barrier, or the cellular membrane of a cancerous or microbial cell, thereby enhancing the therapeutic effectiveness of the active agent. Preferably the drug transporter protein is a member of the ABC superfamily. The drug transporter may either be a multidrug resistance protein (MDR) or a multidrug resistance-associated protein (MRP). The predominant difference between MDR proteins and MRPs is that MRPs require glutathione, in addition to ATP, in order to transport compounds across a biological barrier. Further, the range of substrates may vary from one drug transporter protein to another. ABC transporter inhibitors identified according to the invention can increase brain concentrations of co-administered agents that are substrates of the transporters.

However, among the ABC superfamily of drug transporters, there are several closely conserved regions, the WalkerA region, the WalkerB region, and a short consensus sequence (leucine-serine-glycine-glycine-glutamine, or LSGGQ). In particular, the short consensus sequence LSGGQ is found in essentially every known ABC protein. The QSAR analysis of the present invention provides the very surprising result that the opioid receptor antagonists that act as PGP inhibitors bind to this LSGGQ consensus sequence. Thus the present invention defines a strictly conserved inhibition site shared among all ABC drug transporter proteins. Therefore, the opioid receptor antagonists of the present invention will function as an inhibitor of every ABC drug transporter protein that shares the LSGGQ conserved sequence.

Thus, the present invention is based upon the identification of a new class of drug transporter inhibitors. The term "inhibitor of a drug transporter" or "drug transporter inhibitor" refers to a compound that binds to a drug transporter protein and inhibits, i.e., either completely blocks or merely slows, transport of compounds across biological barriers. An "ABC drug transporter inhibitor" refers to an inhibitor of one or more of the proteins in the ABC superfamily of drug transporters. Drugs that inhibit drug transporters can alter the absorption, disposition and elimination of co-administered drugs and can enhance bioavailability or cause unwanted drug-drug interactions. Interaction with drug transporters can be studied using either direct assays of drug transport in polarized cell systems or with indirect assays such as drug-stimulated ATPase activity and inhibition of the transport of fluorescent substrates. Drugs affected by the drug transporter, P-glycoprotein, at the blood-brain barrier include ondasetron, dexamethasone, domperidone, loperamide, doxorubicin, neifinavir, indinevir, sugguinavir, erythromycin, digoxin, vinblastine, paclitaxel, invermectin and cyclosporin. Known inhibitors of P-glycoprotein include ketoconazole, verapamil, quinidine, cyclosporin, digoxin, erythromycin and loperamide. See, e.g., Intl. J. Clin. Pharmacol. Ther. 38:69–74 (1999). The present invention unexpectedly identifies opioid receptor antagonists, such as naloxone, naltrexone and nalmefene, as potent inhibitors of ABC drug transporters, such as P-glycoprotein.

An "opioid receptor antagonist" is an opioid compound or composition including any active metabolite of such compound or composition that in a sufficient amount attenuates (e.g., blocks, inhibits, prevents or competes with) the action of an opioid receptor agonist. An opioid receptor antagonist binds to and blocks (e.g., inhibits) opioid receptors on nociceptive neurons. Opioid receptor antagonists include: naltrexone (marketed in 50 mg dosage forms as ReVia® or Trexan®), nalaxone (marketed as Narcan®, nalmefene, methylnaltrexone, naloxone, methiodide, nalorphine, naloxonazine, nalide, nalmexone, nalbuphine, nalorphine dinicotinate, naltrindole (NTI), naltrindole isothiocyanate (NTII), naltriben (NTB), nor-binaltorphimine (nor-BNI), b-funaltrexamine (b-FNA), BNTX, cyprodime, ICI-174,864, LY117413, MR2266, or an opioid receptor antagonist having the same pentacyclic nucleus as nelmefene, naltrexone, nalorphine, nalbuphine, thebaine, levallorphan, oxymorphone, butorphanol, buprenorphine, levorphanol meptazinol, pentazocine, dezocine, or their pharmacologically effective esters or salts. In some preferred embodiments, the opioid receptor antagonist is naltrexone, nalmefene, naloxone, or mixtures thereof.

In particular, the present invention contemplates enhancing the efficacy of non-opioid CNS-active agents by co-administering the CNS-active agent with an ABC drug transporter inhibitor, including an opioid transporter inhibitor, such as an opioid receptor antagonist. The opioid receptor antagonists, naltrexone, naloxone and nalmefene, are particularly suited for the present invention. The present invention also contemplates enhancing the efficacy of opioid CNS-active agents, such as an opioid receptor agonist, by co-administering the opioid CNS-active agent, with a non-opioid ABC drug transporter inhibitor. Although some inhibitors of PGP are known in the art, many of these are extremely toxic, especially if used repeatedly over a period of time. For example, when used orally, ketoconazole has been associated with hepatic toxicity, including some fatalities. The opioid receptor antagonists, however, historically have limited side effects, particularly at the low concentrations administered in the present invention. Each of the antagonists naltrexone, naloxone and nalmefene have been approved by the FDA for use in antagonistically effect amounts for treatment of opioid overdose and addiction.

As explained in detail in Example 3, below, a quantitative structure-activity relationship (QSAR) analysis of several opioid drug transporter inhibitors of the present invention defines a pharmacophore consisting of two essential hydroxyls (at positions 3 and 14), a nitrogen with an appended hydrophobic region, and electron density at the 6-position of the opioid compounds. According to this defined pharmacophore, drug transporter inhibitors of the invention have the following formula:

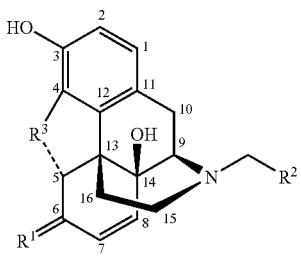

wherein $R^1$ is $CH_2$ or O;
wherein $R^2$ is a cycloalkyl, unsubstituted aromatic, alkyl or alkenyl; and
wherein $R^3$ is O, $CH_2$ or NH.

Most particularly preferred are the opioid receptor antagonists, nalmefene ($R^1$=$CH_2$, $R^2$=cyclopropanyl and $R^3$=O), naloxone ($R^1$=O, $R^2$=ethylene and $R^3$=O) and naltrexone ($R^1$=O, $R^2$=cyclopropanyl and $R^3$=O).

The ABC drug transporter inhibitors, including opioid receptor antagonists according to the invention may be co-administered with any non-opioid CNS-active agent. In addition, opioid CNS-active agents, including opioid receptor agonists, may be co-administered with non-opioid ABC drug transporter inhibitors according to the invention. Opioid receptor agonists may be additionally administered with the co-administered CNS-active agents and the ABC drug transporter inhibitors. The terms "co-administer," "co-administration," "concurrent administration" and "co-treatment" refer to administration of an active agent and a drug transporter inhibitor, in conjunction or combination, together, or before or after each other. The active agent and the drug transporter inhibitor may be administered by different routes. For example, the active agent may be administered orally and the drug transporter inhibitor intravenously, or vice versa. The active agent and the drug transporter inhibitor are preferably both administered orally, as immediate or sustained release formulations. The active agent and drug transporter inhibitor may be administered simultaneously or sequentially, as long as they are given in a manner to allow both agents to achieve effective concentrations to yield their desired therapeutic effects.

As used herein, the term "CNS-active agent" means any therapeutic agent that acts at a site within the central nervous system (CNS), especially within the brain. CNS-active agents include (1) general CNS depressants, such as, anesthetic gases and vapors, aliphatic alcohols, and some hypnotic-sedative drugs; (2) general CNS stimulants, such as pentylenetetrazol, and the methylxanthines; and (3) drugs that selectively modify CNS function, such as anticonvulsants, antiparkinsonism drugs, opioid and non-opioid analgesics, appetite suppressants, antiemetics, analgesic-antipyretics, certain stimulants, antidepressants, antimanic agents, antipsychotic agents, sedatives and hypnotics. The class of CNS-active agents are not limited to agents that act solely within the central nervous system. Examples of CNS-active agents are opioid receptor agonists, such as morphine or oxycodone, which binds to opioid receptors on nociceptive neurons. Examples of non-opioid CNS-active agents include, but are not limited to, valium, lithium, halcyon and ambien.

The amount of an ABC drug transporter inhibitor, such as opioid receptor antagonist, that is necessary to increase the concentration of a co-administered CNS-active agent in the brain will vary from individual to individual. To an extent, the amount of the inhibitor, for example, an opioid receptor antagonist, necessary to achieve the desired effect will also vary from one antagonist to the next. This amount is readily determinable by one skilled in the art according to the invention.

In accordance with the invention, the ABC drug transporter inhibitor, including an opioid inhibitor such as an the opioid receptor antagonist or a non-opioid inhibitor, may be administered with a therapeutically effective amount of the CNS-active agent. "Therapeutic effect" or "therapeutically effective" refers to an effect or effectiveness that is desirable and that is an intended effect associated with the administration of an active agent according to the invention. For example, the therapeutic effect of a CNS-active agent that is an opioid receptor agonist would include analgesia or pain relief or feeling good or calming so as to reduce heart rate, blood pressure or breathing rate. A "therapeutic amount" is the amount of an active agent sufficient to provide a therapeutic effect.

Alternatively, the ABC drug transporter inhibitor, such as an opioid receptor antagonist, may be administered with a sub-therapeutic amount of the CNS-active agent. A "sub-therapeutic amount" is an amount of the active agent that does not cause a therapeutic effect in a patient administered the active agent alone, but when used in combination with the opioid or non-opioid drug transporter inhibitor is therapeutically effective. Co-administering a sub-therapeutic dose of the active agent with the ABC drug transporter inhibitor, such as an opioid receptor antagonist, has many clinical advantages. By administering a smaller amount of the therapeutic agent, it will be possible to obtain the same brain concentration of the active agent while providing a much lower total systemic concentration. This effect will result in fewer system side effects. Further, it is not uncommon for patients to develop tolerance to, dependence upon and/or withdrawal from therapeutic agents over prolonged treatment periods. Administration of sub-therapeutic doses of these tolerance-inducing drugs may keep the level of therapeutic agent below that necessary to develop tolerance, dependence and/or withdrawal symptoms. However, co-administration of an ABC drug transporter inhibitor with a therapeutic or sub-therapeutic dose of a therapeutic agent such as a CNS-active agent, according to the invention enhances efficacy of the agent and/or prevents, attenuates or reverses tolerance to, dependence upon and/or withdrawal from the agent.

An "adverse side effect" of an opioid agonist is a side effect in humans, typically associated with opioid analgesics such as morphine, including nausea vomiting, dizziness, somnolence/sedation, pruritus, reduced gastrointestinal motility including constipation, difficulty in urination, peripheral vasodilation including leading to orthostatic hypotension, headache, dry mouth, sweating, asthenia, dependence, mood changes (e.g., dysphoria, euphoria), or lightheadedness. An "adverse side effect" also includes a serious adverse side effect such as respiratory depression or also apnea, respiratory arrest, circulatory depression, hypotension or shock.

In patients, opioid agonists have been documented to produce numerous adverse side effects. Among the side effects that have been recognized for products containing morphine or other opioid agonists are: respiratory depression; depression of the cough reflex; miosis; reduced gastrointestinal motility including constipation; peripheral vasodilation which may result in orthostatic hypotension; and release of histamine. Adverse side effects that are of particular interest in human subjects include nausea, vomiting, dizziness, headache, somnolence (sedation), and pruritus. Some additional adverse side effects are listed in the Physician Desk Reference (PDR) for selected opioid agonists as follows: morphine: respiratory depression; apnea; circulatory depression; shock respiratory arrest, and cardiac arrest; oxycodone: light-headedness, euphoria, dysphoria, constipation, skin rash; hydrocodone: mental clouding, lethargy, impairment of mental and physical performance, anxiety, fear, dysphoria, dependence, mood changes; constipation; ureteral spasm; spasm of vesical sphincter and urinary retention; and tramadol: seizures; anaphylactoid reactions (lessened resistance to toxins); asthenia; sweating; dyspepsia; dry mouth; diarrhea; CNS stimulation ("CNS stimulation" is a composite that can include nervousness, anxiety, agitation, tremor, spasticity, euphoria, emotional liability and hallucinations); malaise; vasodilation; anxiety, confusion, coordination disturbance, euphoria, nervousness, sleep disorder; abdominal pain, anorexia, flatulence, hypertonia, rash, visual disturbance, menopausal symptoms, urinary frequency, urinary retention.

The invention is based in part upon corresponding relationship between drug transporter protein function and the concentration of the opioid agent in the central nervous system, particularly in the brain. Without being limited to a particular theory, it is believed that the increase in brain concentrations is mediated by inhibition of active transport of the CNS-active agents by P-glycoprotein. The agents cross the blood brain barrier according to normal physiological paths, e.g., diffusion of lipophilic molecules across the cell membrane of the endothelial cells lining the cerebral capillaries. Once across the blood brain barrier, the agent is captured by the drug transporter protein and swept back to the exterior side of the blood brain barrier. Thus the active efflux of therapeutic agents results in an artificially low concentration of the agent within the central nervous system, particularly in the brain. As described in Example 3, some drug transporter inhibitors such as nalmefene and naltrexone additionally inhibit the ATPase activity of an ABC transporter protein and thereby may also increase influx of drugs through the ABC proteins transmembrane channel. Accordingly, increased brain concentrations of CNS-active agents that are ABC protein substrates may be achieved either through inhibiting active efflux by the ABC protein, or through increasing influx, for example, by inhibiting the associated ATPase and thus allowing passage through the ABC protein, or by a combination of both decreasing efflux and increasing influx.

As described in detail in the Examples below, co-administration of an opioid CNS-active agent, such as morphine, and a drug transporter inhibitor, such as naltrexone, results in a higher concentration of morphine in the brain as compared to that found in a subject who received morphine alone. Thus one aspect of the present invention provides methods of increasing the efficacy of opioid CNS-active agents by co-administering a CNS-active agent with an amount of a drug transporter inhibitor (e.g., a non-opioid inhibitor) effective to increase the concentration of the opioid agent in the brain.

Without being bound by a theory of the invention, it is believed that by reducing efflux and/or enhancing influx via modulation of an ABC drug transporter and/or drug transporter-associated ATPase activity, that it is possible to maintain sufficient intracerebral concentrations of the therapeutic agent to provide therapeutic benefit while avoiding adverse side effects. Specifically with regard to opioid CNS-active agents, it is possible to avoid depletion of the central store of endogenous opioids within the brain. Thus the adverse side effects of tolerance, dependence and/or withdrawal are avoided by the present invention and the beneficial effects of enhanced efficacy and/or reduced toxicity is provided by the present invention.

The term "opioid" refers to compounds or compositions including metabolites of such compounds or compositions which bind to specific opioid receptors and have agonist (activation) or antagonist (inactivation) effects at these receptors, and thus are "opioid receptor agonists" or "opioid receptor antagonists." These include opioid alkaloids, such as the agonist morphine and its metabolite morphine-6-glucuronide and the antagonist naltrexone and its metabolite and opioid peptides, including enkephalins, dynorphins and endorphins. The opioid can be present as a member selected from an opioid base and an opioid pharmaceutically acceptable salt. The pharmaceutically acceptable salt embraces an inorganic or an organic salt. Representative salts include hydrobromide, hydrochloride, mutate, succinate, n-oxide, sulfate, malonate, acetate, phosphate dibasic, phosphate monobasic, acetate trihydrate, bi(heplafluorobutyrate), maleate, bi(methylcarbamate), bi(pentafluoropropionate), mesylate, bi(pyridine-3-carboxylate), bi(trifluoroacetate), bitartrate, chlorhydrate, fumarate and sulfate pentahydrate. The term "opiate" refers to drugs derived from opium or related analogs. A "non-opioid CNS-active agent" is a CNS-active agent, as defined above, that does not bind to specific opioid receptors or if it binds one that fails to activate or inactivate the receptor.

Many opioid CNS-active agents are opioid receptor agonists. An "opioid receptor agonist" is an opioid compound or composition including any active metabolite of such compound or composition that binds to and activates opioid receptors on nociceptive neurons, which mediate pain. Such opioid receptor agonists have analgesic activity (with measurable onset, peak, duration and/or total effect) and can product analgesia. Opioid receptor agonists according to the present invention include: alfentanil, allylprodine, alphaprodine, anileridine, apomorphine, apocodeine, benzylmorphine, bezitramide, buprenorphine, butorphanol, clonitazene, codeine, cyclazocine, cyclorphen, cyprenorphine, desomorphine, dextromoramide, dezocine, diampromide, dihydrocodeine, dihyrdomorphine, dimenoxadol, dimepheptanol, dimethylthiambutene, dioxyaphetyl butyrate, dipipanone, eptazocine, ethoheptazine, ethylmethylthiambutene, ethylmorphine, etonitazene, fentanyl, heroin, hydrocodone, hydroxymethylmorphinan, hydromorphone, hydroxypethidine, isomethadone, ketobemidone, levallorphan, levorphanol, levophenacylmorphan, lofentanil, meperidine, meptazinol, metazocine, methadone, methylmorphine, metopon, morphine, myrophine, nalbuphine, narceine, nicomorphine, norlevorphanol, normethadone, nalorphine, normorphine, norpipanone, ohmefentanyl, opium, oxycodone, oxymorphone, papaveretum, pentazocine, phenadoxone, phenomorphan, phenazocine, phenoperidine, pholcodine, piminodine, piritramide, propheptazine, promedol, profadol, properidine, propiram, propoxyphene, remifenanyl, sufentanyl, tramadol, tilidine, salts thereof, mixtures of any of the foregoing, mixed mu-agonists/antagonists, mu-antagonist combinations, or the like. Preferred opioid receptor agonists for human use include morphine, hydrocodone, oxycodone, codeine, fentanyl (and its relatives), hydromorphone, meperidine, methadone, oxymorphone, propoxyphene or tramadol, or mixtures thereof. Particularly preferred agonists include morphine, oxycodone, hydrocodone or tramadol. Opioid receptor agonists include exogenous or endogenous opioids.

As a compound that activates opioid receptors on nociceptive neurons, opioid receptor agonists are commonly used as analgesic agents. "Analgesia" refers to the attenuation, reduction or absence of sensibility to pain, including the provision of pain relief, the enhancement of pain relief, or the attenuation of pain intensity. An "analgesic" amount refers to an amount of the opioid receptor agonist which causes analgesia in a subject administered the opioid receptor agonist alone, and includes standard doses of the agonist which are typically administered to cause analgesia (i.e., mg doses). An "analgesic" amount refers to an amount that results in analgesic efficacy, for example, as measured by a subject with a pain relief score or a pain intensity difference score, at a given timepoint, or over time, or as compared to a baseline, and includes calculations based on area under the curve (AUC) such as TOTPAR or SPID from such pain relief scores or pain intensity difference scores. A "hypo-analgesic" amount is a less-than-analgesic amount, including an amount which is not analgesic or is weakly analgesic in a subject administered the opioid receptor agonist alone, and further includes an "anti-analgesic" or "algesic" amount which is an amount which increases pain. A "sub-analgesic" amount is an amount that does not cause analgesia in a subject administered the opioid receptor agonist alone, but when used in combination with the opioid receptor antagonist, results in analgesia.

For administration to human subjects or in the treatment of any clinical conditions, the pharmaceutical compositions or dosage forms of this invention may be utilized in compositions such as capsules, tablets or pills for oral administration, suppositories for rectal administration, liquid compositions for parenteral administration and the like.

The pharmaceutical compositions or dosage forms of this invention may be used in the form of a pharmaceutical preparation, for example, in solid or semisolid form, which contains one or more of the drug transporter inhibitors, as an active ingredient, alone, or in combination with one or more therapeutic agents. Any drug transporter inhibitor or therapeutic agent may be in admixture with an organic or inorganic carrier or excipient suitable for external, enteral or parenteral applications. The drug transporter inhibitor may be compounded, for example, with the usual non-toxic, pharmaceutically acceptable carriers for capsules, tablets, pellets, suppositories, and any other form suitable for use. The carriers which can be used are water, glucose, lactose, gum acacia, gelatin, mannitol, starch paste, magnesium, trisilicate, talc, corn starch, keratin, colloidal silica, potato starch, urea and other carriers suitable for use in manufacturing preparations, in solid or semisolid form, and in addition auxiliary, stabilizing, thickening and coloring agents and perfumes may be used. The drug transporter inhibitor, alone or in conjunction with a therapeutic agent, is included in the pharmaceutical composition or dosage form in an amount sufficient to produce the desired effect upon the process or condition, including a variety of conditions and diseases in humans.

For preparing solid compositions such as tablets, the drug transporter inhibitor, alone or in conjunction with therapeutic agent, is mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the present invention, or a non-toxic pharmaceutically acceptable salt thereof. When referring to these preformulation compositions as homogeneous, it is meant that the drug transporter inhibitor, alone or in conjunction with therapeutic agent, is dispersed evenly throughout the composition so that the composition may be readily subdivided into equally effective unit dosage forms such as capsules, tablets, caplets, or pills. The capsules, tablets, caplets, or pills of the novel pharmaceutical composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate. Controlled release (e.g., slow-release or sustained-release) dosage forms, as well as immediate release dosage forms are specifically contemplated according to the present invention.

Compositions in liquid forms in which a therapeutic agent may be incorporated for administration orally or by injection include aqueous solution, suitable flavored syrups, aqueous or oil suspensions, and emulsions with acceptable oils such as cottonseed oil, sesame oil, coconut oil or peanut oil, or with a solubilizing or emulsifying agent suitable for intravenous use, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Compositions for inhalation or insufflation include solutions and suspensions in pharmaceutically acceptable, aqueous or organic solvents, or mixtures thereof, and powders. The liquid or solid compositions may contain suitable pharmaceutical Iv acceptable excipients as set out above. Preferably the compositions are administered by the oral or nasal respiratory route for local or systemic effect. Compositions in preferably sterile pharmaceutically acceptable solvents may be nebulized by use of inert gases. Nebulized solutions may be breathed directly from the nebulizing device or the nebulizing device may be attached to a face mask, tent or intermittent positive pressure breathing machine. Solution, suspension or powder compositions may be administered, preferably orally or nasally, from devices which deliver the formulation in an appropriate manner.

A drug transporter inhibitor alone, or in combination with a therapeutic agent, may be administered to the human subject by known procedures including but not limited to oral, sublingual, intramuscular, subcutaneous, intravenous, intratracheal, transmucosal, or transdermal modes of administration. When a combination of these compounds are administered, they may be administered together in the same composition, or may be administered in separate compositions. If the therapeutic agent and the drug transporter inhibitor are administered in separate compositions, they may be administered by similar or different modes of administration, or may be administered simultaneously with one another, or shortly before or after the other.

The drug transporter inhibitors alone, or in combination with therapeutic agents are formulated in compositions with a pharmaceutically acceptable carrier ("pharmaceutical compositions"). The carrier must be "acceptable" in the sense of being compatible with the other ingredients of the formulation and not deleterious to the recipient thereof.

Examples of suitable pharmaceutical carriers include lactose, sucrose, starch, talc, magnesium stearate, crystalline cellulose, methyl cellulose, carboxymethyl cellulose, glycerin, sodium alginate, gum arabic, powders, saline, water, among others. The formulations may conveniently be presented in unit dosage and may be prepared by methods well-known in the pharmaceutical art, by bringing the active compound into association with a carrier or diluent, or optionally with one or more accessory ingredients, e.g., buffers, flavoring agents, surface active agents, or the like. The choice of carrier will depend upon the route of administration. The pharmaceutical compositions may be administered as solid or semisolid formulations, including as capsules, tablets, caplets, pills or patches. Formulations may be presented as an immediate-release or as a controlled-release (e.g., slow-release or sustained-release) formulation, including, for example, methadone hydrochloride, Dolophine (Roxane); Methadose (Mallinkrodt); hydrocodone bitartrate and acetaminophen (Vicodin, Knoll Labs); Lortab (UCB); oxycodone hydrochloride, OxyContin, sustained release (Purdue); tramadol (Ultram, Johnson & Johnson); meperidine hydrochloride (Demerol, Sanofi); hydromorphone hydrochloride (Dilaudid, Knoll Labs); codeine sulfate (Roxane); or propoxyphene hydrochloride (Darvon, Lilly).

For oral or sublingual administration, the formulation may be presented as capsules, tablets, caplets, powders, granules or a suspension, with conventional additives such as lactose, mannitol, corn starch or potato starch; with binders such as crystalline cellulose, cellulose derivatives, acacia, corn starch, gelatins, natural sugars such as glucose or beta-lactose, corn sweeteners, natural and synthetic gums such as acacia, tragacanth, or sodium alginate, carboxymethylcellulose, polyethylene glycol, waxes, or the like; with disintegrators such as corn starch, potato starch, methyl cellulose, agar, bentonite, xanthan gums, sodium carboxymethyl-cellulose or the like; or with lubricants such as talc, sodium oleate, sodium stearate, magnesium stearate, sodium benzoate, sodium acetate, sodium chloride or the like.

For transdermal administration, the compounds may be combined with skin penetration enhancers such as propylene glycol, polyethylene glycol, isopropanol, ethanol, oleic acid, N-methylpyrrolidone, or the like, which increase the permeability of the skin to the compounds, and permit the compounds to penetrate through the skin and into the bloodstream. The compound/enhancer compositions also may be combined additionally with a polymeric substance such as ethylcellulose, hydroxypropyl cellulose, ethylene/vinylacetate, polyvinyl pyrrolidone, or the like, to provide the composition in gel form, which can be dissolved in solvent such as methylene chloride, evaporated to the desired viscosity, and then applied to backing material to provide a patch.

For intravenous, intramuscular, or subcutaneous administration, the compounds may combined with a sterile aqueous solution which is preferably isotonic with the blood of the recipient. Such formulations may be prepared by dissolving solid active ingredient in water containing physiologically compatible substances such as sodium chloride, glycine, or the like, and/or having a buffered pH compatible with physiological conditions to produce an aqueous solution, and/or rendering said solution sterile. The formulations may be present in unit or multi-dose containers such as sealed ampoules or vials.

When the drug transporter inhibitor is used in combination with the therapeutic agent, the amount of the therapeutic agent administered may be a therapeutic or sub-therapeutic amount. As used herein, a "therapeutic" amount is the amount of the therapeutic agent which causes a therapeutic effect in a subject administered the therapeutic agent alone. The amount of the drug transporter inhibitor may be an amount effective to enhance the therapeutic potency of and/or attenuate the adverse side effects of the therapeutic agent. The optimum amounts of the drug transporter inhibitor administered alone or in combination with a therapeutic agent will of course depend upon the particular drug transporter inhibitor and therapeutic agent used, the carrier chosen, the route of administration, and/or the pharmacokinetic properties of the subject being treated.

When the drug transporter inhibitor is administered alone, the amount of the drug transporter inhibitor administered is an amount effective to enhance or maintain the therapeutic potency of the therapeutic agent and/or attenuate or maintain the adverse side effects of the therapeutic agent. This amount is readily determinable by one skilled in the art according to the invention.

Compounds can be tested in vitro for their ability to serve as inhibitors of drug transporter proteins. Cells expressing a drug transporter, such as P-glycoprotein, are suitable for use in in vitro screens. Details of an appropriate protocol for testing compounds for their ability to inhibit PGP-associated drug transport are given in the Examples. The method described involves growing a monolayer of PGP-expressing cells in such a manner as to present PGP on only one face of the monolayer, then applying a known PGP substrate and the test substance to the PGP-presenting side of the monolayer. After a period of incubation, the level of PGP substrate is measured on the non-PGP-presenting side of the monolayer. Inhibition of the drug transporter protein is characterized by a decreased concentration of PGP substrate on the non-PGP-presenting side of the monolayer as compared to the concentration found if the experiment is performed in the absence of test substrate.

Alternatively, inhibitors of drug transporter proteins can be identified by assaying for ATPase activity. In this type of assay, the ability of the test substrate to inhibit the ATPase activity of a drug transporter activated by a known substrate is examined. The test substances are incubated with ABC drug transporter containing-membranes and supplemented with MgATP, with and without sodium orthovanadate present. Orthovanadate inhibits PGP by trapping MgADP in the nucleotide binding site. Thus, the ATPase activity measured in the presence of orthovanadate represents non-PGP ATPase activity and was subtracted from the activity generated without orthovanadate to yield vanadate-sensitive ATPase activity.

Use of these screening protocols would result in identification of compounds that can modulate the activity of drug transporter proteins at the blood brain barrier. Accordingly, these compound would also be expected to decrease the efflux of therapeutic agents from the brain.

The present invention is described in the following examples which are set forth to aid in the understanding of the invention, and should not be construed to limit in any way the invention as defined in the claims which follow thereafter.

EXAMPLES

Example 1

Opioid Receptor Antagonists Inhibit Human PGP-Mediated Transport

Porcine kidney-derived, LLC-PK$_1$, cells expressing human PGP cDNA (designated 15B-J) were cultured in 24 well Transwell™ culture inserts at 37° C. on an orbital shaker. Transport assays were conducted in 24 well Transwell™ culture inserts with Hanks Balanced Salt Solution (HBSS) buffered with the addition of 10 mM HEPES (pH 7.2).

The test substances, naloxone, naltrexone and nalmefene, were purchased from Sigma-Aldrich. Stock solutions of the compounds were made in DMSO, and dilutions of these in transport buffer were prepared for assay in the monolayers. The DMSO concentration (0.55%) was constant for all conditions within the experiment. All test substance and control drug solutions prepared in HBSS/HEPES buffer contained 0.55% DMSO.

The test substance was added to the donor and receiver chambers. Duplicate monolayers and thirteen test substance concentrations of 0.0001, 0.0003, 0.001, 0.003, 0.01, 0.03, 0.1, 0.3, 1.0, 3.0, 10, 30 and 100 μM were used. PGP substrate [$^3$H]-digoxin, at 5 μM was added to the donor chamber (either the apical or basolateral chamber depending on the direction of transport). After an incubation time of 90 minutes, a sample from the receiver chamber was analyzed for the amount of digoxin present. The positive control for inhibition was 25 μM ketoconazole added to donor and receiver chambers with 5 μM [$^3$H]-digoxin added to the donor chamber. The negative control for inhibition was 5 μM [$^3$H]-digoxin added to the donor chamber (either the apical or basolateral chamber depending on the direction of transport) with Hanks Balanced Salt Solution (HBSS) buffered with the addition of 10 mM HEPES (pH 7.2) and DMSO at 0.55% in the receiver chamber.

The rate of digoxin transported from the apical chamber to the basolateral chamber (A to B) and from the basolateral chamber to the apical chamber (B to A) was measured and apparent permeability $P_{app}$ constants calculated. The polarization ratio $P_{app\ B\ to\ A}/P_{app\ A}$ was calculated. A lower polarization ratio in the 15B-J cells with test substance relative to that without test substance provides evidence for inhibition of PGP-mediated digoxin transport by the test substance. Transport of 5 μM [3H]-digoxin was measured following coincubation with the test substances at nominal concentrations in the range of 0 to 100 μM. Inhibition of digoxin transport was calculated by comparison of the digoxin polarization ratio in the presence of the test substance, to the ratio in the absence of test substance. The positive control for inhibition was 25 μM ketoconazole coincubated with digoxin. The inhibition of PGP-mediated transport in human PGP-expressing porcine kidney cell monolayers by naloxone is summarized in Table 1.

TABLE 1

Naloxone inhibition of PGP-mediated transport

| Naloxone Concentration (μM) | | Digoxin Polarization Ratio | % Inhibition of Digoxin | Ketoconazole Normalized % Inhibition of |
|---|---|---|---|---|
| nominal | measured | (B–A/A–B) | Transport | Digoxin Transport |
| 0 | — | 3.7 | — | — |
| 0.0001 | 0.000021 | 3.5 | 4.4 | 6.2 |
| 0.0003 | 0.000138 | 3.5 | 6.0 | 8.4 |
| 0.001 | 0.00085 | 3.4 | 7.3 | 10 |
| 0.03 | 0.0021 | 3.6 | 4.0 | 5.7 |
| 0.01 | 0.0083 | 3.8 | -3.2 | -4.5 |
| 0.03 | 0.021 | 3.5 | 4.1 | 5.7 |
| 0.1 | 0.074 | 3.8 | -1.9 | -2.7 |
| 0.3 | 0.264 | 3.3 | 11.9 | 17 |
| 1 | 1.04 | 3.5 | 5.5 | 7.8 |

The inhibition of PGP-mediated transport in human PGP-expressing porcine kidney cell monolayers by naltrexone is summarized in Table 2.

TABLE 2

Naltrexone inhibition of PGP-mediated transport

| Concentration Naltrexone (μM) | Polarization ratio (B–A/A–B) | % Inhibition of Digoxin Transport | Ketoconazole Normalized % Inhibition of Digoxin Transport |
|---|---|---|---|
| 0 | 4.0 | — | — |
| 0.0001 | 3.6 | 10 | |
| 0.0003 | 3.5 | 14 | |
| 0.001 | 3.6 | 10 | |
| 0.003 | 3.7 | 8 | |
| 0.01 | 3.5 | 11 | |
| 0.03 | 3.8 | 5 | |
| 0.1 | 3.5 | 14 | |
| 0.3 | 3.3 | 18 | |
| 1.0 | 3.4 | 14 | |

The inhibition of PGP-mediated transport in human PGP-expressing porcine kidney cell monolayers by nalmefene is summarized in Table 3.

TABLE 3

Nalmefene inhibition of PGP-mediated transport

| Concentration Nalmefene (μM) | Polarization Ratio (B–A/A–B) | % Inhibition of Digoxin Transport | Ketoconazole Normalized % Inhibition of Digoxin Transport |
|---|---|---|---|
| 0 | 4.5 | — | — |
| 0.0001 | 4.3 | 5.2 | |
| 0.0003 | 4.2 | 7.2 | |
| 0.001 | 4.4 | 2.8 | |
| 0.003 | 4.3 | 5.1 | |
| 0.01 | 4.3 | 3.9 | |
| 0.03 | 4.8 | -7.2 | |
| 0.1 | 4.5 | -0.3 | |
| 0.3 | 4.8 | -5.6 | |
| 1.0 | 4.6 | -2.6 | |

Naloxone and naltrexone exhibited inhibitory behavior at the 30 and 100 μM concentrations. Digoxin transport appears to have been slightly inhibited at naloxone and naltrexone concentrations below 30 μM, however the inhibition was not concentration-dependent. Digoxin transport was increasingly inhibited in response to increasing concentration of nalmefene at concentrations between 3 and 100 μM. The positive control, 25 μM ketoconazole, inhibited digoxin transport within the accepted range, indicating that the cell model performed as expected.

Example 2

6-β-Naltrexol Does Not Inhibit Human PGP-Mediated Transport

Porcine kidney-derived, LLC-PK$_1$, cells expressing human PGP cDNA (designated 15B-J) were cultured in 24 well Transwell™ culture inserts at 37° C. on an orbital shaker. Transport assays were conducted in 24 well Transwell™ culture inserts with Hanks Balanced Salt Solution (HBSS) buffered with the addition of 10 mM HEPES (pH 7.2).

The test substance, 6-β-naltrexol, was provided by LC Resources, Inc. Stock solutions of the compounds were made in DMSO, and dilutions of these in transport buffer were prepared for assay in the monolayers. The DMSO concentration (0.55%) was constant for all conditions within the experiment. All test substance and control drug solutions prepared in HBSS/HEPES buffer contained 0.55% DMSO.

The test substance was added to the donor and receiver chambers. Duplicate monolayers and thirteen test substance concentrations of 0.0001, 0.0003, 0.001, 0.003, 0.01, 0.03, 0.1, 0.3, 1, 3, 10, 30 and 100 μM, were used. PGP substrate [$^3$H]-digoxin, at 5 μM was added to the donor chamber (either the apical or basolateral chamber depending on the direction of transport). After an incubation time of 90 minutes, a sample from the receiver chamber was analyzed for the amount of digoxin present. The positive control for inhibition was 25 μM ketoconazole added to donor and receiver chambers with 5 μM [$^3$H]-digoxin added to the donor chamber. The negative control for inhibition was 5 μM [$^3$H]-digoxin added to the donor chamber (either the apical or basolateral chamber depending on the direction of transport) and Hanks Balanced Salt Solution (HBSS) buffered with the addition of 10 mM HEPES (pH 7.2) and DMSO at 0.55% in the receiver chamber.

Transport of 5 μM [$^3$H]-digoxin was measured following coincubation with test substance 6-β-naltrexol, at nominal concentrations in the range of 0 to 100 μM. Inhibition of digoxin transport was calculated by comparison of the digoxin polarization ratio in the presence of the test substance, to the ratio in the absence of test substance. The positive control for inhibition was 25 μM ketoconazole coincubated with digoxin.

Digoxin efflux in the human PGP-expressing cell monolayers was slightly inhibited (mean of 8.5+/−7.1%) by 6-β-naltrexol in the concentration range of 0.0001 to 30 μM (Table 4 The inhibition did not appear to be concentration-dependent. At 100 μM 6-β-naltrexol, however, digoxin transport was more strongly inhibited (28%). The positive control, 25 μM ketoconazole, inhibited digoxin transport within the accepted range, indicating that the cell model performed as expected.

TABLE 4

6-β-naltrexol inhibition of PGP-mediated transport

| Nominal concentration of 6-β-naltrexol | Polarization Ratio (B−A/A−B) | % Inhibition of Digoxin Transport |
|---|---|---|
| 0 | 4.7 | — |
| 0.0001 | 4.4 | 6.4 |
| 0.0003 | 4.7 | 0 |
| 0.001 | 4.8 | −2.1 |
| 0.003 | 4.7 | 0 |
| 0.01 | 4.6 | 2.1 |
| 0.03 | 4.2 | 11 |
| 0.1 | 3.8 | 19 |
| 0.3 | 4.3 | 9 |
| 1.0 | 4.0 | 15 |
| 3.0 | 4.2 | 11 |
| 10 | 4.0 | 15 |
| 30 | 4.0 | 15 |
| 100 | 3.4 | 28 |
| 25 μM Ketoconazole | 1.0 | 79 |

The test substance 6-β-naltrexol was not a potent inhibitor of PGP-mediated digoxin transport, in the concentration range tested.

Example 3

Opioid Receptor Antagonists Inhibit PGP ATPase Activity

The test substances, naloxone, naltrexone and nalmefene, were purchased from Sigma-Aldrich. Stock solutions of the compounds were made in DMSO, and dilutions of these in transport buffer were prepared for assay in the monolayers. The DMSO concentration (0.55%) was constant for all conditions within the experiment. All test substance and control drug solutions prepared in HBSS/HEPES buffer contained 0.55% DMSO.

The test substances were incubated in the membranes and supplemented with MgATP, with and without sodium orthovanadate present. Orthovanadate inhibits PGP by trapping MgADP in the nucleotide binding site. Thus, the ATPase activity measured in the presence of orthovanadate represents non-PGP ATPase activity and was subtracted from the activity generated without orthovanadate to yield vanadate-sensitive ATPase activity.

ATPase assays were conducted in 96-well microtiter plates. A 0.06 ml reaction mixture containing 40 μg PGP membranes, test substance, and 4 mM MgATP, in buffer containing 50 mM Tris-MES, 2 mM EGTA, 50 mM KCl, 2 mM dithiothreitol, and 5 mM sodium azide, plus organic solvent was incubated at 37° C. for 20 minutes. Triplicate incubations of ten test substance concentrations (of 0.003, 0.01, 0.03, 0.1, 0.3, 1.0, 3.0, 10, 30 and 100 μM) and the test vehicle without drug, were used. Identical reaction mixtures containing 100 μM sodium orthovanadate were assayed in parallel. The reactions were stopped by the addition of 30 μl of 10% SDS+Antifoam A. The incubations were followed with addition of 200 μl of 35 mM Ammonium Molybdate in 15 mM Zinc Acetate:10% Ascorbic Acid (1:4) and incubated for an additional 20 minutes at 37° C. Additionally, 0.06 ml aliquots of potassium phosphate standards prepared in the buffer described above, were incubated in the plates containing the test and control substances, with SDS and detection reagent added. The liberation of inorganic phosphate was detected by its absorbance at 800 nm and quantitated by comparing the absorbance to a phosphate standard curve. The concentration dependence of the PGP was analyzed for evidence of saturation of PGP-ATPase activity, and apparent kinetic parameters were calculated by non-linear regression. The positive control for stimulation of ATPase activity was 20 μM verapamil, and the positive control for inhibition of basal ATPase activity was 25 mM ketoconazole.

In a semi-quantitative assay for ATPase inhibition, Naltrexone, Naloxone and Nalmefene were shown to inhibit the ATPase associated with PGP1a as shown in Table 5.

TABLE 5

Vanadate-sensitive ATPase Activity

| Concentration | Activity (nmol/mg min) | | |
|---|---|---|---|
| (μM) | Naloxone | Naltrexone | Nalmefene |
| 100 | 1.8 | 4.6 | 3.2 |
| 30 | 1.9 | — | 2.3 |
| 10 | 2 | — | — |
| 3 | 1.7 | — | — |
| 1 | 0.4 | — | — |

The order of inhibition of the PgP1a associated ATPase was nalmefene, naltrexone and naloxone. Naloxone only weakly inhibited the PGP1a associated ATPase. None of the compounds were stimulators of ATPase.

Example 4

Molecular Modeling of ABC Transporter Inhibitors

A molecular modeling analysis was performed on a series of compounds, including opioid analogues, to elucidate their mode of interaction with PGP1a, and to determine, if possible, a pharmacophore for drug transporter inhibitors useful according to the present invention. Exemplary compounds in this study were naltrexone, naloxone, nalmefene, 6-β-naltrexol and nalorphine. The structures of compounds are illustrated in FIG. 1. The compounds are structurally very similar, and exhibit two measured activities. "Activity 1" is characterized by a low capacity, high affinity binding site with activity ranging from 0.3 nM to greater than 200 μM. On the other hand, "activity 2" is characterized by a high capacity, low affinity binding site with activity ranging from 10 μM to greater than 100 μM. Table 6 provides the biological activities for each of the exemplary compounds.

TABLE 6

Biological Activity of Exemplary Compounds

| Compound | Activity 1 | Activity 2 |
|---|---|---|
| Nalmefene | 0.3 nM | 100 μM |
| Naltrexone | 0.3 nM | 100 μM |
| Naloxone | 1.0 nM | 30 μM |
| 6-β-Naltrexol | 0.1 nM | 100 μM |
| Nalorphine | N/A | N/A |

In performing the calculations for the molecular modeling analysis, two assumptions were made. First, nalorphine exhibits no measurable activity. Second, the structures of the compounds as represented in the Merck Index represent the active form of the compound.

An important difference in these compounds is that nalorphine lacks the hydroxyl group in the central ring at position 14 (see, e.g., FIG. 1), indicating that this hydroxyl group is a requirement for activity. The most active compounds (nalmefene and naltrexone) each have a hydrophobic group (cyclopropyl) tethered to the nitrogen, indicating that a hydrophobic moiety is partially responsible for the higher activity in these compounds. This moiety may be viewed as a necessary, but not sufficient condition, since several of the inactive compounds also possess this hydrophobic region. Initial activity data suggest that the electron density present at this location in naloxone (due to the ethylene substituent [C=C]) is contributory to its lower activity. The observation that 6-β-Naltrexol is even less active is attributed to the hydroxyl substituent at the 6 position being oriented β to the ring system, perhaps penetrating a sterically limited region in the receptor.

In summary, the analysis indicates that the presence of the hydroxyl group at the 14-position may be required for activity, since nalorphine, with no measured activity, lacks this moiety. In addition, the two most active compounds (nalmefene and naltrexone) possess an ethylene group and a carbonyl group respectively at the 6-position. This may represent a requirement for electron density at this position, rather than a hydrogen-bond acceptor site, as there is only a one order of magnitude difference in activity (0.3 nM vs. 3 nM) between the ethylene group (nalmefene) and the carbonyl group (naltrexone). There is a potential steric limit for substituent size or directionality at the 6-position. 6-β-Naltrexol places its hydroxyl group in a direction that penetrates into this region. Finally, a hydrophobic group is required as the N-substituent for highest activity, as naloxone, with a double bond rather than the cyclopropyl group, exhibits significantly lower activity.

When the novel analysis described above is now considered in conjunction with a recent scientific article investigated the ability of a variety of peptidomimetic thrombin inhibitors to inhibit intestinal transport [Kamm et al., "Transport of peptidomimetic thrombin inhibitors with a 3-amino-phenylalanine structure: permeability and efflux mechanism in monolayers of a human intestinal cell line (Caco-2)." Pharm. Res. 18:1110-8 (2001)], it is possible to utilize additional structural information from Kamm to perform additional analyses and modeling. Kamm et al. proposed that basic and acidic residues of amidino-henylalanine-derived thrombin inhibitors mediate affinity to intestinal efflux pumps, presumably PGP and MRP. Structural information from Kamm et al. useful in the novel QSAR analysis of the present invention is summarized below.

TABLE 7

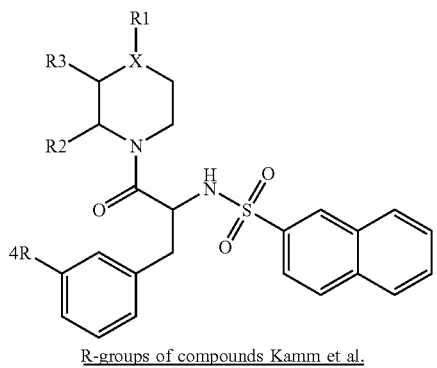

R-groups of compounds Kamm et al.

| Structure | R1 | R2 | R3 | X | R4 |
|---|---|---|---|---|---|
| 1 | Me | H | H | C | NH₂ / NH (amidine) |
| 2 | H | COOH | H | C | NH₂ / NH (amidine) |
| 3 | H | COO—Me | H | C | NH₂ / NH (amidine) |
| 4 | H | H | COOH | C | NH₂ / NH (amidine) |
| 5 | H | H | COO—Me | C | NH₂ / NH (amidine) |
| 6 | COOH | H | H | C | NH₂ / NH (amidine) |
| 7 | COO—Me | H | H | C | NH₂ / NH (amidine) |
| 8 | COOH | H | H | C | HN—OH / NH (hydroxyamidine) |

TABLE 7-continued

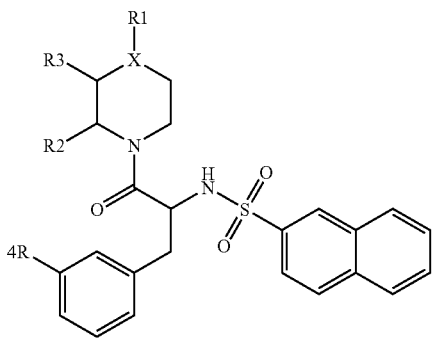

R-groups of compounds Kamm et al.

| Structure | R1 | R2 | R3 | X | R4 |
|---|---|---|---|---|---|
| 9 | COOH | H | H | C | HN-C(Me)=NH (NH) |
| 10 | H | H | H | N | NH$_2$-C=NH (NH) |
| 11 | C(O)Me | H | H | N | NH$_2$-C=NH (NH) |
| (12) | Me | H | H | C | NH$_2$-C=NH (NH) |
| 13 | Me | H | H | C | NH$_2$ |
| 14 | Me | H | H | C | —CH$_2$NH$_2$ |
| 15 | Me | H | H | C | HN-C(OH)=NH (NH) |
| 16 | Me | H | H | C | HN-C(Me)=NH (NH) |

The intestinal permeability coefficients of the Kamm compounds were studied using Caco-2 monolayers and reverse-phase HPLC method for quantitation. Further the efflux ratios (transport from B to A:transport from A to B) were calculated. The efflux ratios for a selection of the Kamm compounds measured at 250 µM are provided in Table 8.

TABLE 8

Efflux Ratios at 250 µM

| Structure | Efflux Ratio B→A/A→B |
|---|---|
| 1 | 45.0 |
| 2 | 2.8 |

TABLE 8-continued

Efflux Ratios at 250 µM

| Structure | Efflux Ratio B→A/A→B |
|---|---|
| 3 | 10.5 |
| 4 | 2.7 |
| 5 | 11.1 |
| 6 | 1.9 |
| 7 | 6.0 |
| 8 | 22.1 |
| 9 | 1.1 |
| 10 | 0.8 |
| 11 | 2.4 |

The efflux ratios the remaining Kamm compounds measured at 100 µM are provided in Table 9.

TABLE 9

Efflux Ratios at 100 µM

| Structure | Efflux Ratio B→A/A→B |
|---|---|
| 1 | 16.3 |
| 12 | 24.9 |
| 13 | 1.14 |
| 14 | 3.43 |
| 15 | 1.31 |
| 16 | 13.0 |

Comparable measurements for the opioid analogues are provided in Table 10. The data of Table 10 was obtained from the experiments described in Example 1. Efflux ratios normalized to 25 µM ketoconazole (Keto) are presented in parentheses after the measured ratios.

TABLE 10

Efflux Ratios of Opioid Analogues

| Structure | Keto @ 25 µM | Activity 1 | | Activity 2 | |
|---|---|---|---|---|---|
| | | [C] µM | B→A/A→B | [C] µM | B→A/A→B |
| Nalmefene | 1.4 | 0.0003 | 4.2 (3.0) | 100 | 2.6 (1.9) |
| Naltrexone | 1.0 | 0.0003 | 3.5 (3.5) | 100 | 2.7 (2.7) |
| Naloxone | 1.1 | 0.001 | 3.4 (3.1) | 30 | 2.6 (2.4) |
| Naloxone | | | | 100 | 2.7 (2.5) |
| 6-β-Naltrexol | 1.0 | 0.0001 | 4.4 (4.4) | 100 | 3.4 (3.4) |

An overlay of the opioid analogue structures is presented in FIG. 2. All active ("Activity 1") compounds share the following features: two hydroxyl groups (a) at positions 3 and 14, a furan ring system, a hydrophobic region in ring system, a region of electron density at position 6 (b), and a cyclic tertiary nitrogen (c) with an appended hydrophobic group (d).

Figure 3A:
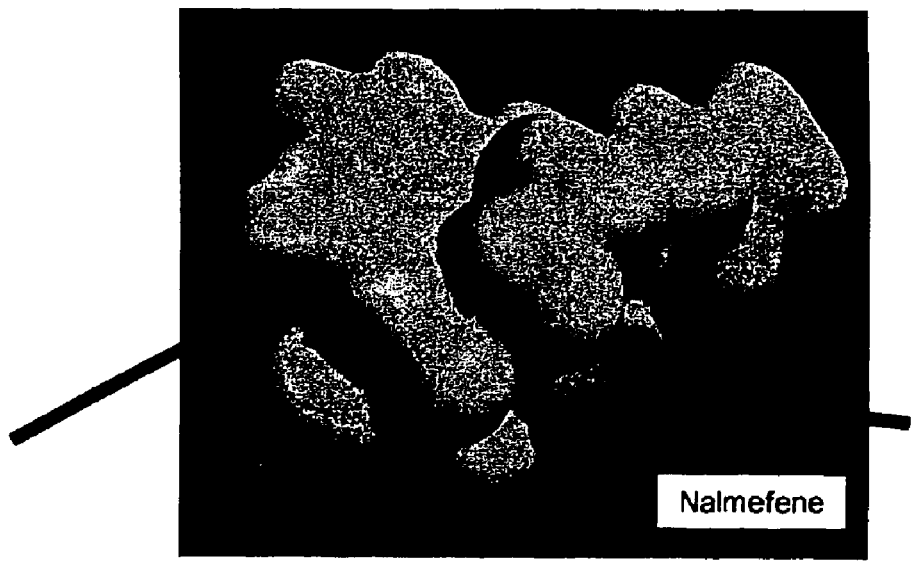
FIG. 3A shows the molecular orbitals and electrostatic potential of nalmefene as calculated using Spartan (Wavefunction, Inc.).

Molecular Orbital calculations were performed on the compounds using Spartan (Wavefunction, Inc.). There were no appreciable differences among the active compounds with respect to their electrostatic potentials. The electrostatic potential of nalmefene and naloxone are illustrated in FIGS. 3A and B respectively. The arrows indicate the hydroxyl group hydrogen-bond donor sites noted above.

Figure 3B:
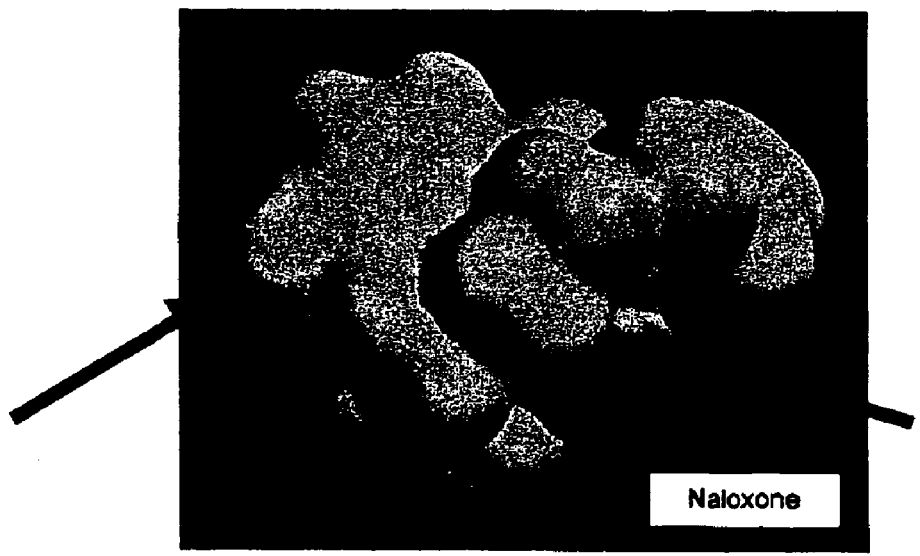
FIG. 3B shows the molecular orbitals and electrostatic potential of naloxone as calculated using Spartan (Wavefunction, Inc.).

Two views of an overlay of nalmefene and the low energy conformer of Kamm Compound 1 was prepared. The ring stacking structure predicted by Confort for the Kamm compounds embodies a conserved hydrophobic region shared by the both the Kamm compounds and the exemplary opioid compounds. The hydrogen-bond donor sites noted in the FIG. 3 are overlap the predicted hydrogen bonding sites of the Kamm compound. The nalmefene furan ring oxygen overlays on an aromatic ring in Kamm Compound 1, suggesting that the oxygen atom is not necessary for this activity.

In silico analyses of chemical compounds were conducted as follows. Diversity estimations were made on nalmefene, naloxone, naltrexone, 6-β-naltrexol, and the 16 Kamm et al structures using DiverseSolutions software from Tripos (R. S. Pearlman, UT-Austin). A chemistry space defined by approximately 900,000 chemical entities (several commercially available databases of compounds) was used as a reference. The commercial databases used as sources of the 900,000 chemical entities were MDL Information Systems (http://www.mdli.com), ACD Database (http://www.mdli.com/cgi/dynamic/product.html?uid=$uid&key=$key&id=17), NCI (http://dtp.nci.nih.gov/docs/3d_database/structural_information/smiles_strings.html), Aldrich (http://www.sigma-aldrich.com/saws.nsf/home?openframeset), ASINEx Ltd. (http://www.asinex.com), and Chemstar (http://www.chemstar.ru). A transporter-relevant subspace was determined based on the former chemistry space, using the "B→A/A→B" efflux ratios to represent the activities. In order to have sufficient data, the Kamm et al data was combined with the high affinity/low capacity data provided for the exemplary opioid compounds. The 200 "nearest neighbors" are listed in Table 11 below. Note that in the Receptor-Relevant Subspace, the active compounds are focused in a small region of the overall chemistry space.

TABLE 11

200 Nearest Neighbors

| Rank | Database I.D. # | Distance to Exemplary compound | | |
|---|---|---|---|---|
| 1 | 70413 | 0.0096 | to | Naloxone |
| 2 | MFCD00133650 | 0.0184 | to | Nalmefene |
| 3 | 349115 | 0.4061 | to | Nalmefene |
| 4 | BAS 3387173 | 0.5101 | to | Naloxone |
| 5 | BAS 1002455 | 0.5195 | to | Naloxone |
| 6 | BAS 3387155 | 0.5243 | to | Naloxone |
| 7 | BAS 1268016 | 0.5345 | to | Naloxone |
| 8 | BAS 3387156 | 0.5412 | to | Naloxone |
| 9 | BAS 3387130 | 0.5462 | to | Naloxone |
| 10 | MFCD01935543 | 0.5507 | to | Naloxone |
| 11 | 688277 | 0.5913 | to | 6-β-Naltrexol |
| 12 | BAS 1002441 | 0.6179 | to | Naloxone |
| 13 | BAS 3386059 | 0.6369 | to | Naloxone |
| 14 | BAS 1003176 | 0.6370 | to | Naloxone |
| 15 | BAS 1004848 | 0.6434 | to | Naloxone |
| 16 | MFCD00273259 | 0.6436 | to | Nalmefene |
| 17 | MFCD00273270 | 0.6458 | to | Naloxone |
| 18 | MFCD00273266 | 0.6482 | to | Naloxone |
| 19 | BAS 3386023 | 0.6526 | to | Naloxone |
| 20 | BAS 2026128 | 0.6569 | to | Naloxone |
| 21 | 617005 | 0.6581 | to | 6-β-Naltrexol |
| 22 | MFCD00079194 | 0.6622 | to | 6-β-Naltrexol |
| 23 | 19045 | 0.6665 | to | 6-β-Naltrexol |
| 24 | 76021 | 0.6733 | to | Nalmefene |
| 25 | BAS 1002442 | 0.6770 | to | Naloxone |
| 26 | MFCD00271723 | 0.6822 | to | Naloxone |
| 27 | MFCD00273273 | 0.6884 | to | Nalmefene |
| 28 | MFCD00273264 | 0.6968 | to | Nalmefene |
| 29 | BAS 2026145 | 0.6977 | to | Naloxone |
| 30 | BAS 3387114 | 0.7036 | to | Naloxone |
| 31 | 376679 | 0.7051 | to | Naltrexone |
| 32 | 379963 | 0.7051 | to | Naltrexone |
| 33 | 157870 | 0.7144 | to | Nalmefene |
| 34 | MFCD00273274 | 0.7198 | to | Naloxone |
| 35 | MFCD00273260 | 0.7228 | to | Nalmefene |
| 36 | BAS 1003163 | 0.7272 | to | Naloxone |
| 37 | BAS 1003182 | 0.7388 | to | Naltrexone |
| 38 | BAS 0510629 | 0.7564 | to | Naltrexone |
| 39 | BAS 1002419 | 0.7571 | to | Naloxone |
| 40 | 18579 | 0.7600 | to | Nalmefene |
| 41 | 58796 | 0.7600 | to | Nalmefene |
| 42 | BAS 1004835 | 0.7634 | to | Naloxone |
| 43 | BAS 2004373 | 0.7646 | to | Naloxone |
| 44 | 693856 | 0.7680 | to | Nalmefene |
| 45 | MFCD01764789 | 0.7687 | to | Naloxone |
| 46 | MFCD00271738 | 0.7719 | to | Nalmefene |
| 47 | BAS 2025996 | 0.7741 | to | Naloxone |
| 48 | BAS 2282169 | 0.7798 | to | Nalmefene |
| 49 | MFCD00273268 | 0.7895 | to | Naloxone |
| 50 | MFCD00179880 | 0.7997 | to | Naloxone |
| 51 | BAS 1507170 | 0.8014 | to | Nalmefene |
| 52 | BAS 3386088 | 0.8017 | to | Naloxone |
| 53 | MFCD00272082 | 0.8183 | to | Nalmefene |
| 54 | MFCD00271113 | 0.8289 | to | 6-β-Naltrexol |
| 55 | 116054 | 0.8308 | to | 6-β-Naltrexol |
| 56 | BAS 1004837 | 0.8352 | to | Naloxone |
| 57 | 134536 | 0.8364 | to | 6-β-Naltrexol |
| 58 | 615801 | 0.8556 | to | Naltrexone |
| 59 | 404374 | 0.8695 | to | Nalmefene |
| 60 | MFCD00273318 | 0.8697 | to | Nalmefene |
| 61 | MFCD00271094 | 0.8774 | to | Nalmefene |
| 62 | 202587 | 0.8895 | to | Nalmefene |
| 63 | 693862 | 0.8919 | to | Nalmefene |
| 64 | MFCD00467140 | 0.9049 | to | Nalmefene |
| 65 | 693863 | 0.9093 | to | Naltrexone |
| 66 | MFCD00271196 | 0.9123 | to | Nalmefene |
| 67 | BAS 3386092 | 0.9195 | to | Naloxone |
| 68 | 693855 | 0.9235 | to | Nalmefene |
| 69 | BAS 3386091 | 0.9278 | to | Naloxone |
| 70 | MFCD00665833 | 0.9291 | to | Naltrexone |
| 71 | 404368 | 0.9412 | to | 6-β-Naltrexol |
| 72 | BAS 0606820 | 0.9478 | to | Naloxone |
| 73 | 693859 | 0.9485 | to | Nalmefene |
| 74 | BAS 0436353 | 0.9653 | to | Naloxone |
| 75 | MFCD00167445 | 0.9681 | to | Naltrexone |
| 76 | MFCD00667402 | 0.9742 | to | Nalmefene |
| 77 | MFCD002258126 | 0.9767 | to | Naloxone |
| 78 | MFCD00143186 | 0.9850 | to | Naltrexone |
| 79 | 119887 | 0.9932 | to | Naloxone |
| 80 | 404365 | 1.0016 | to | Nalmefene |
| 81 | MFCD01871411 | 1.0116 | to | Naloxone |
| 82 | 152720 | 1.0147 | to | 6-β-Naltrexol |
| 83 | 117581 | 1.0164 | to | Naloxone |
| 84 | 669466 | 1.0171 | to | Naloxone |
| 85 | MFCD00271129 | 1.0287 | to | Nalmefene |
| 86 | 689431 | 1.0350 | to | 6-β-Naltrexol |
| 87 | MFCD00056772 | 1.0390 | to | Nalmefene |
| 88 | MFCD00199295 | 1.0449 | to | Nalmefene |
| 89 | R191469 | 1.0457 | to | Nalmefene |
| 90 | 375504 | 1.0503 | to | Naloxone |
| 91 | 692397 | 1.0656 | to | Naloxone |
| 92 | MFCD00433684 | 1.0691 | to | Naloxone |
| 93 | 693860 | 1.0709 | to | Nalmefene |
| 94 | MFCD01764791 | 1.0725 | to | Naloxone |
| 95 | BAS 1519270 | 1.0776 | to | Naloxone |
| 96 | BAS 3385849 | 1.0828 | to | Naloxone |
| 97 | MFCD00673308 | 1.0866 | to | Nalmefene |
| 98 | 404356 | 1.0990 | to | Nalmefene |
| 99 | 43938 | 1.1067 | to | Nalmefene |
| 100 | 117181 | 1.1092 | to | Naltrexone |
| 101 | MFCD00094379 | 1.1109 | to | Nalmefene |
| 102 | 404369 | 1.1109 | to | 6-β-Naltrexol |
| 103 | 381577 | 1.1111 | to | Naloxone |
| 104 | S842214 | 1.1117 | to | Nalmefene |
| 105 | 134602 | 1.1123 | to | 6-β-Naltrexol |
| 108 | CHS 0316796 | 1.1130 | to | Naloxone |

TABLE 11-continued

200 Nearest Neighbors

| Rank | Database I.D. # | Distance to | | Exemplary compound |
|---|---|---|---|---|
| 107 | 134604 | 1.1147 | to | Nalmefene |
| 108 | R171697 | 1.1334 | to | Nalmefene |
| 109 | MFCD00667401 | 1.1343 | to | Nalmefene |
| 110 | S959863 | 1.1367 | to | 6-β-Naltrexol |
| 111 | 35545 | 1.1369 | to | 6-β-Naltrexol |
| 112 | 134598 | 1.1369 | to | 6-β-Naltrexol |
| 113 | S310778 | 1.1403 | to | Naloxone |
| 114 | 669800 | 1.1408 | to | Naloxone |
| 115 | BAS 0083962 | 1.1413 | to | Naltrexone |
| 116 | MFCD01765597 | 1.1424 | to | 6-β-Naltrexol |
| 117 | 682334 | 1.1427 | to | Naloxone |
| 118 | BAS 0631739 | 1.1428 | to | Nalmefene |
| 119 | MFCD00144882 | 1.1486 | to | 6-β-Naltrexol |
| 120 | MFCD00229975 | 1.1497 | to | Naloxone |
| 121 | R171700 | 1.1568 | to | Nalmefene |
| 122 | 134592 | 1.1633 | to | 6-β-Naltrexol |
| 123 | 401210 | 1.1662 | to | Nalmefene |
| 124 | BAS 2026074 | 1.1715 | to | Naltrexone |
| 125 | BAS 3050727 | 1.1767 | to | Nalmefene |
| 126 | BAS 0341630 | 1.1851 | to | Naloxone |
| 127 | 97817 | 1.1901 | to | Naloxone |
| 128 | ASN 3185453 | 1.1958 | to | Naloxone |
| 129 | 21257 | 1.1962 | to | 6-β-Naltrexol |
| 130 | 134601 | 1.2005 | to | 6-β-Naltrexol |
| 131 | BAS 2026075 | 1.2027 | to | 6-β-Naltrexol |
| 132 | BAS 1996620 | 1.2114 | to | 6-β-Naltrexol |
| 133 | MFCD01314356 | 1.2147 | to | Naloxone |
| 134 | BAS 2026097 | 1.2207 | to | Naltrexone |
| 135 | BAS 1914007 | 1.2210 | to | Naloxone |
| 136 | CHS 0003221 | 1.2266 | to | Naloxone |
| 137 | 667258 | 1.2274 | to | Naloxone |
| 138 | 37625 | 1.2351 | to | Nalmefene |
| 139 | BAS 1003093 | 1.2362 | to | 6-β-Naltrexol |
| 140 | 16468 | 1.2380 | to | Naloxone |
| 141 | CHS 0227049 | 1.2409 | to | Naloxone |
| 142 | BAS 0315050 | 1.2410 | to | Nalmefene |
| 143 | BAS 1289763 | 1.2421 | to | Naloxone |
| 144 | 349127 | 1.2429 | to | Naloxone |
| 145 | 635928 | 1.2496 | to | Nalmefene |
| 146 | BAS 2377555 | 1.2507 | to | 6-β-Naltrexol |
| 147 | MFCD00665835 | 1.2508 | to | Naltrexone |
| 148 | 47931 | 1.2547 | to | 6-β-Naltrexol |
| 149 | 76435 | 1.2572 | to | Nalmefene |
| 150 | 90558 | 1.2581 | to | Naloxone |
| 151 | MFCD00206273 | 1.2608 | to | Naloxone |
| 152 | 159208 | 1.2670 | to | Nalmefene |
| 153 | BAS 0341580 | 1.2672 | to | Naltrexone |
| 154 | BAS 2377575 | 1.2678 | to | Naltrexone |
| 155 | MFCD01765638 | 1.2681 | to | Nalmefene |
| 156 | R171484 | 1.2684 | to | Nalmefene |
| 157 | 700350 | 1.2716 | to | Naloxone |
| 158 | 16907 | 1.2740 | to | Nalmefene |
| 159 | R170623 | 1.2754 | to | Nalmefene |
| 160 | S98907 | 1.2776 | to | Naloxone |
| 161 | 10464 | 1.2777 | to | Naloxone |
| 162 | 215214 | 1.2777 | to | Naloxone |
| 163 | R171425 | 1.2802 | to | Nalmefene |
| 164 | MFCD00153032 | 1.2831 | to | 6-β-Naltrexol |
| 165 | S196991 | 1.2850 | to | Naltrexone |
| 166 | R170291 | 1.2863 | to | Naloxone |
| 167 | 682335 | 1.2867 | to | Naloxone |
| 168 | UFCD00667377 | 1.2889 | to | Nalmefene |
| 169 | 106242 | 1.2944 | to | Naloxone |
| 170 | R170410 | 1.2989 | to | Naloxone |
| 171 | MFCD0005912 | 1.2996 | to | Naloxone |
| 172 | MFCD01765637 | 1.3018 | to | Nalmefene |
| 173 | 376678 | 1.3028 | to | Naltrexone |
| 174 | MFCD01314431 | 1.3031 | to | Naloxone |
| 175 | 370278 | 1.3040 | to | Nalmefene |
| 176 | MFCD00242635 | 1.3054 | to | 6-β-Naltrexol |
| 177 | S602965 | 1.3058 | to | Naltrexone |
| 178 | 370279 | 1.3063 | to | Nalmefene |
| 179 | 157877 | 1.3099 | to | Nalmefene |
| 180 | 19046 | 1.3103 | to | 6-β-Naltrexol |
| 181 | 117862 | 1.3103 | to | 6-β-Naltrexol |
| 182 | MFCD00667305 | 1.3134 | to | Nalmefene |
| 183 | MFCD00667382 | 1.3161 | to | Nalmefene |
| 184 | 611276 | 1.3178 | to | 6-β-Naltrexol |
| 185 | BAS 1099232 | 1.3197 | to | Naltrexone |
| 186 | BAS 0313319 | 1.3206 | to | 6-β-Naltrexol |
| 187 | 401211 | 1.3254 | to | Nalmefene |
| 188 | 409635 | 1.3263 | to | Nalmefene |
| 189 | 106231 | 1.3271 | to | Naloxone |
| 190 | 375505 | 1.3289 | to | Naloxone |
| 191 | BAS 1053035 | 1.3309 | to | Naloxone |
| 192 | ASN 3160807 | 1.3316 | to | Naloxone |
| 193 | 324633 | 1.3331 | to | Naloxone |
| 194 | 370277 | 1.3392 | to | Naloxone |
| 195 | MFCD00375811 | 1.3428 | to | 6-β-Naltrexol |
| 196 | CHS 0305736 | 1.3435 | to | 6-β-Naltrexol |
| 197 | BAS 0659522 | 1.3435 | to | 6-β-Naltrexol |
| 198 | 381576 | 1.3461 | to | Naloxone |
| 199 | CHS 0120289 | 1.3484 | to | Naloxone |
| 200 | 351159 | 1.3490 | to | Nalmefene |

A pharmacophore for a drug transporter inhibitor useful according to the present invention contains the hydroxyl groups at the 14-position and 3-position as discussed above, the nitrogen, hydrophobic region (tethered to the nitrogen), and the region of electron density at the 6-position. Other combinations of features are also possible as discussed below.

The distance between the hydroxuyl groups in the pharmacophore ("H" of OH to "H" of OH) is approximately 7.4 Å. The equivalent distance in "Kamm 1" is ~7.7 Å. These distances are to the Hydrogen atoms, rather than the H-bond acceptors in the binding site. The N-substituent lengths of nalmefene (from N to terminal Carbons) are ~3.9 Å and ~3.5 Å. N-substituent length of naloxone (from N to terminal Carbon) is ~3.4 Å.

The three-dimensional coordinates of naltrexone are provided in Table 12.

TABLE 12

Three-dimensional coordinates

| ATOM | X | Y | Z | Type | Charge |
|---|---|---|---|---|---|
| C1 | −0.0352 | −0.1951 | 0.0725 | C. ar | 0.1489 |
| C2 | 2.0834 | −0.0915 | 0.6474 | C. 3 | 0.1387 |
| C3 | 2.3288 | 1.3986 | 0.5409 | C. 2 | 0.1298 |
| C4 | 2.7343 | 2.1393 | 1.7840 | C. 3 | 0.0249 |
| C5 | 1.6213 | 1.9380 | 2.8395 | C. 3 | −0.0154 |
| C6 | 1.5391 | 0.4338 | 3.2099 | C. 3 | 0.0664 |
| C7 | 1.2934 | −0.4401 | 1.9514 | C. 3 | 0.0294 |
| C8 | 0.3791 | 0.1181 | 4.2040 | C. 3 | 0.0429 |
| C9 | −1.0383 | 0.5073 | 3.6641 | C. 3 | 0.0052 |
| C10 | −1.2030 | 0.2284 | 2.1659 | C. ar | −0.0334 |
| C11 | −0.0782 | −0.1163 | 1.4337 | C. ar | −0.0151 |
| C12 | −2.4171 | 0.3074 | 1.4505 | C. ar | −0.0499 |
| C13 | −2.4130 | 0.2019 | 0.0328 | C. ar | −0.0203 |
| C14 | −1.2074 | 0.0000 | −0.6793 | C. ar | 0.1404 |
| O15 | 1.2170 | −0.4755 | −0.4637 | O. 3 | −0.2867 |
| C16 | 1.3253 | −1.9545 | 2.2801 | C. 3 | −0.0592 |
| N17 | 0.4895 | −1.3246 | 4.5611 | N. 3 | −0.2960 |
| C18 | 0.3363 | −2.2765 | 3.4315 | C. 3 | −0.0091 |
| O19 | 2.8028 | 0.1380 | 3.8337 | O. 3 | −0.3969 |
| O20 | −1.1968 | 0.0000 | −2.0760 | O. 3 | 0.3351 |
| O21 | 2.1919 | 2.0008 | −0.5126 | O. 2 | −0.3894 |
| C22 | −0.1632 | −1.7771 | 5.8169 | C. 3 | 0.0022 |

TABLE 12-continued

Three-dimensional coordinates

| ATOM | X | Y | Z | Type | Charge |
|------|------|------|------|------|--------|
| C23 | 0.2667 | −0.9142 | 7.0296 | C. 3 | −0.0282 |
| C24 | −0.5945 | −1.0908 | 8.2998 | C. 3 | −0.0488 |
| C25 | −0.7018 | 0.2063 | 7.4700 | C. 3 | −0.0488 |
| H26 | −3.3439 | 0.2757 | −0.5190 | H | 0.0719 |
| H27 | −3.3515 | 0.4481 | 1.9839 | H | 0.0519 |
| H28 | −0.7033 | −2.2458 | 3.0686 | H | 0.0417 |
| H29 | 0.5379 | −3.3100 | 3.7583 | H | 0.0417 |
| H30 | 1.0537 | −2.5464 | 1.3901 | H | 0.0165 |
| H31 | 2.3491 | −2.2448 | 2.5610 | H | 0.0165 |
| H32 | 3.7066 | 1.7640 | 2.1382 | H | 0.0495 |
| H33 | 2.8430 | 3.2119 | 1.5551 | H | 0.0495 |
| H34 | 0.6739 | 2.3152 | 2.4251 | H | 0.0308 |
| H35 | 1.8585 | 2.5217 | 3.7437 | H | 0.0308 |
| H36 | −1.2074 | 1.5867 | 3.7999 | H | 0.0488 |
| H37 | −1.8236 | −0.0234 | 4.2195 | H | 0.0488 |
| H38 | 3.0581 | −0.5987 | 0.5948 | H | 0.0780 |
| H39 | 0.5866 | 0.7227 | 5.1003 | H | 0.0510 |
| H40 | −0.3069 | 0.0000 | −2.4176 | H | 0.2424 |
| H41 | 2.8163 | −0.7158 | 4.2555 | H | 0.2089 |
| H42 | 0.1871 | −2.7925 | 6.0602 | H | 0.0429 |
| H43 | −1.2569 | −1.8218 | 5.7021 | H | 0.0429 |
| H44 | 1.3391 | −0.7446 | 7.2194 | H | 0.0313 |
| H45 | −1.6257 | 0.3467 | 6.8884 | H | 0.0268 |
| H46 | −0.2477 | 1.1098 | 7.9059 | H | 0.0268 |
| H47 | −1.4559 | −1.7752 | 8.2529 | H | 0.0268 |
| H48 | −0.0805 | −1.0045 | 9.2699 | H | 0.0268 |

Through the use of these coordinates a pharmacophore may be defined by: (1) a hydrogen bonding moiety at a three-dimensional location corresponding to the hydroxyl at position 3 of naltrexone; (2) a hydrogen bonding moiety at a three-dimensional location corresponding to the hydroxyl at position 14 of naltrexone; (3) a hydrophobic moiety at a three-dimensional location corresponding to the cyclopropyl moiety appended to the nitrogen of naltrexone; and (4) a region of electron density at a three-dimensional location corresponding to the ethylene moiety at 6-position of naltrexone.

Example 5

Morphine Pharmacokinetics in Blood and Brain of Rats Studied with Microdialysis A study of the brain pharmacokinetics of morphine was performed in a three day study in each rat. A total of 9 successful rats per group were required (70% success rate= 13 rats per group). Each group was divided into two parts; 4 animals received an morphine dose for three days, and 5 animals received an morphine dose the first day and combined morphine-naltrexone doses on Days 2 and 3.

Of the rats, 3 individuals of each gender were decapitated at the end of the first day (1 from M1 and F1 and 2 from M2 and F2, respectively). 3 rats of each gender (M2 and F2) were decapitated right after the infusion on day 4 for collection of whole brain (necessary for brain volume of distribution measurements).

In a first experiment, after a stabilization period of at least five days in the animal house, the animals were anaesthetized by inhalation of Enfluran®. Two indwelling cannulae, PE-10 connected to PE-50, were implanted into the femoral artery for blood sampling and into the femoral vein for drug infusion. A heparinized saline solution (100 IU/ml) was maintained in the arterial cannulae to prevent clotting. All ends of the catheters were passed subcutaneously to a plastic cup placed on the surface of the neck out of reach from the rat. Two stainless steel sutures are placed in the tail of the rat 1 and 3 cm from the root of the tail for the analgesic measurements. The rat is placed in a CMA/120 system for freely moving animals with free access to water and food, and the experiment started approximately 24 hours later. All experiments started at the same time of the day.

Each rat was weighed (range 270–330 g). The baseline for antinociception was measured three times with 15-minute intervals before the start of the experiment. During the procedure all rats were held gently in a towel. The duration of the stimuli was 1 sec, using a frequency of electrical square waves of 125 pulses/sec and a pulse width of 1.6 msec. The voltage was increased in logarithmic steps. A vocalization response was recorded as the endpoint, the pain threshold. The maximal voltage accepted was 11.5 V.

Figure 5:
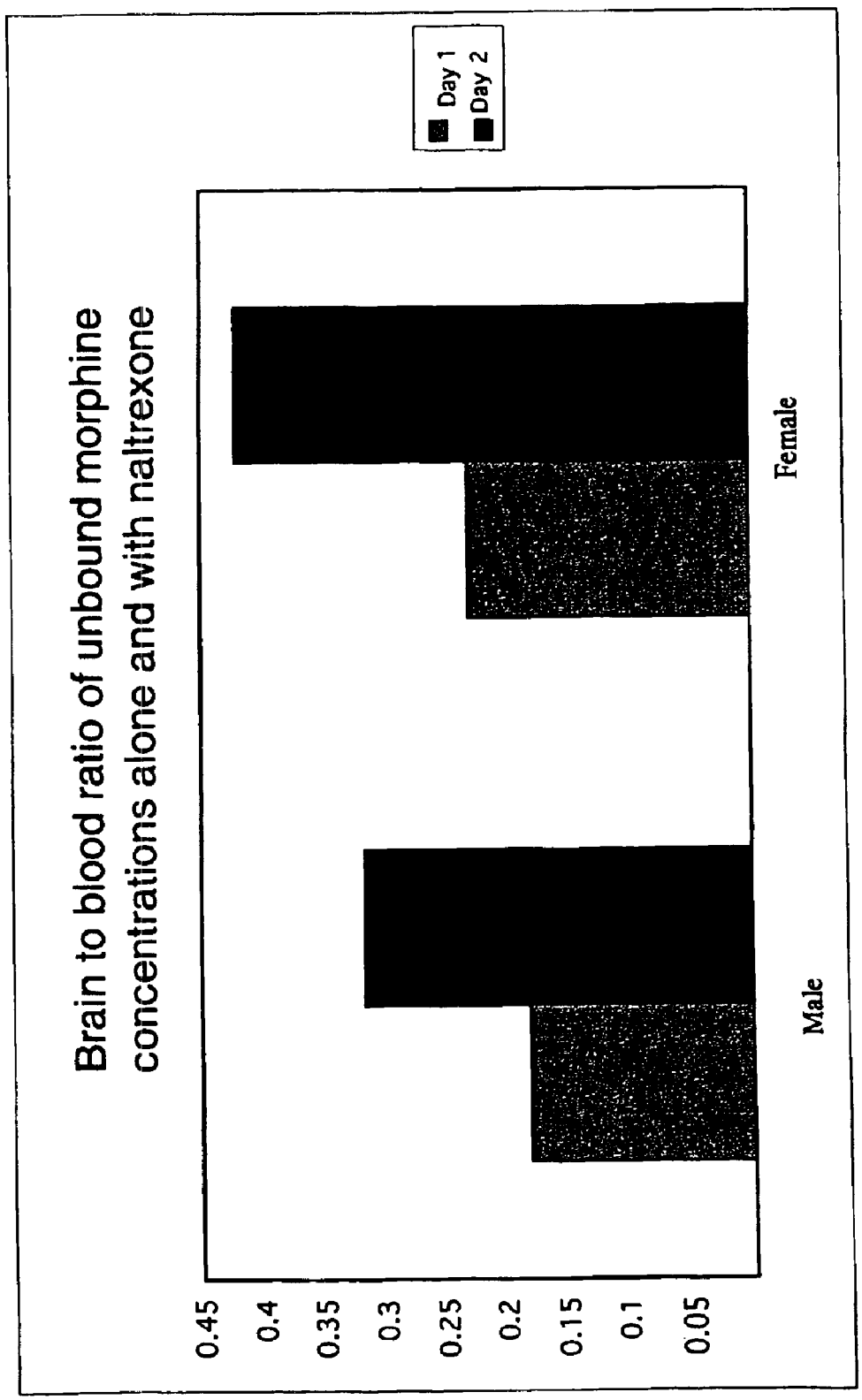
FIG. 5 illustrates the effect of naltrexone on the concentration of morphine in the brain of male and female rats.

Morphine was administered as an intravenous infusion over 10 minutes at an infusion rate of 1.8 mg/kg/h (0.1 mg/kg) and 18 mg/kg/h (1 mg/kg). 200 µl blood samples were collected at 5, 10, 15, 20, 40, 60, 120, 240 and 300 min from the start of the 10-minute infusion. All blood samples were centrifuged at 5,000 rpm for 5 minutes, and the plasma harvested and stored at −20° C. until analyzed. Antinociception was measured 5, 10, 15, 20, 30, 45, 60 min after the start of the infusion and thereafter every 30 minutes up to 240 min. The ratio of brain concentration of morphine to blood concentration of morphine is shown the FIG. 5.

In a second experiment, after a stabilization period of at least five days in the animal house, the animals are anaesthetized by inhalation of Enfluran®. Two indwelling cannulae, PE-10 connected to PE-50, were implanted into the femoral artery for blood sampling and into the femoral vein for drug infusion. A heparinised saline solution (100 IU/ml) was maintained in the arterial cannulae to prevent clotting. The blood probe (CMA/20) was inserted into the right jugular vein through a guide cannulae and fixed to the pectoralis muscle with two sutures. The rat was placed in a stereotaxic instrument for the implantation of the striatal probe. A midline incision was made to expose the skull and the CMA/12 guide cannulae was implanted into the striatum with the co-ordinates 2.7 mm lateral and 0.8 mm anterior to the bregma, and 3.8 mm ventral to the surface of the brain. The brain probe was inserted into the hole and fixed with a screw and dental cement. A 15 cm PE-50 tubing was looped subcutaneously on the back of the rat to the surface of the neck in order to let the perfusion solution adjust to body temperature before entering the brain probe. All ends of the catheters were passed subcutaneously to a plastic cup placed on the surface of the neck out of reach from the rat. Two stainless steel sutures were placed in the tail of the rat 1 and 3 cm from the root of the tail for the analgesic measurements. The rat was placed in a CMA/120 system for freely moving animals with free access to water and food, and the experiment started approximately 24 hours later. All experiments started at the same time of the day.

Each rat was weighed (range 270–330 g). The probes were perfused with blank Ringer's solution at a flow rate of 1 µl/min. Microdialysate fractions were collected every 15 minutes for 1 hour. After a 60 min stabilization period the microdialysis probes were perfused with an morphine solution containing 100 ng/ml (blood) or 200 ng/ml (striatum). Unbound concentrations of morphine were calculated from the dialysate concentration of morphine adjusted for the in vivo recovery value. After the retrodialysis period, the probes were perfused for one hour with blank perfusion solution.

The rats were randomly assigned into two groups receiving an i.v. infusion of morphine hydrochloride over 10 min.

Groups M1 and F1 (n=8) were administered 2 mg/kg morphine given with buffer to achieve the same volume as groups M2 and F2. Groups M2 and F2 (n=10) which receive the same dose MS as groups M1 and F1 plus a chosen dose of NTX.

After the infusion was stopped at Day 1, one rat from M1 and F1 and two rats from M2 and F2 were decapitated. The brain was divided into two parts and each part put in a plastic cup and stored at −70° C. until analyzed. The remaining animals proceeded with the study.

Microdialysates were collected over a period of 240 min into pre-weighed vials. Samples were taken at 5 min intervals during the infusion, at 10 min intervals over the following hour and at 15 min intervals over the remaining 3 hours. Dialysates were collected, weighed and stored at −20° C. until analyzed. Arterial blood samples (200 ul) were collected in heparinised vials at 0, 8, 20, 70, 130, 190 and 240 min. After collection, samples were centrifuged at 5000 rpm for 5 min, and plasma was harvested and frozen at −20° C. until analysis.

Antinociception was measured according to the electrical stimulation vocalization method. An electrical stimulus was applied to the two electrodes implanted in the tail of the rat. During the procedure all rats were held gently in a towel. The duration of the stimuli was 1 sec, using a frequency of electrical square waves of 125 pulses/sec and a pulse width of 1.6 msec. The voltage was increased in logarithmic steps. A vocalization response was recorded as the endpoint, the pain threshold. The maximal voltage accepted was 11.5 V. The baseline value of the pain threshold was estimated three times at 15 min intervals before the start of the experiment. Antinociception was recorded at the end of the blank, retrodialysis and washout periods and at 5, 10, 15, 20, 30, 45, 60 min after the start of the infusion and thereafter every 30 minutes up to 240 min.

The blood gas status of the rats was monitored by injection of a 50 µl arterial blood sample into a blood gas analyzer to determine the arterial $pO_2$, $pCO_2$, $O_2$ saturation and pH. During the experiment the blood gas status was monitored just before antinociception measurement.

On Day 4, each rat was weighed (range 270–330 g). The probes were perfused with blank Ringer's solution at a flow rate of 1 µl/min. Microdialysate fractions were collected every 15 minutes for 1 hour. After a 60 min stabilization period the microdialysis probes were perfused with an morphine solution containing 100 ng/ml (blood) or 200 ng/ml (striatum). Unbound concentrations of morphine were calculated from the dialysate concentration of morphine adjusted for the in vivo recovery value. After the retrodialysis period, the probes were perfused for one hour with blank perfusion solution.

The rats received an i.v. infusion over 10 minutes of morphine hydrochloride or morphine and naltrexone as determined above. After the infusion was stopped at Day 4, the remaining three rats of groups M2 and F2 were decapitated, directly after directly after morphine and NTX administration. The brain was divided into two parts and each part put in a plastic cup and stored at −70° C. until analyzed.

Example 6

Tolerance and Withdrawal in Mice 40 male mice were randomized into 5 groups of eight. All mice were administered single 3 mg/kg morphine daily (b.i.d.), beginning on Day 1. The anti-nociceptive effect was assayed by standard tail flick procedures for mice in Group 1 on Days 1, 3, 5, 8, 10 and 12. The mice in Groups 2–5 were assayed on Days 5, 8, 10 and 12. Groups 2, 3, 4 and 5 received daily doses of 3 ng/kg, 30 ng/kg, 300 ng/kg and 3000 ng/kg naltrexone (b.i.d.), respectively, beginning at day 6. Anti-nociceptive effect was assayed by tail flick on Days 5 (prior to naltrexone dosing), 6, 8, and 10.

The mice in Group 1 showed adaptation to the repeated dosing of morphine. The data were subjected to two types of analyses; cross sectional time series analysis using generalized estimating equations (GEE) and survival analysis using Cox regression. The Cox and GEE analyses of Group 1 were consistent and showed that the latency (time to tail flick) was shorter after day 1. The Cox analysis showed that although Day was the major factor influencing latency, Time periods after 60 minutes also significantly influenced latency. Note it could be argued that reduced latency after day 1 is an adaptation to the morphine or an adaptation by the mice to having repeated tail flick experiments conducted on them. However, since all groups of mice had similar tail flick responses on day 5 and this is despite the fact that four groups (groups 2–5) experienced the tail flick experiment for first time, this can be interpreted as evidence that reduced latency after day 1 is due to adaptation to morphine.

The change in latency within a day (day 1) of group 1 mice was analyzed. At all times after time zero, the latency was significantly different from that measured at time zero.

The variability between groups of mice were compared at Day 5. Very little difference existed between groups in terms of their latency. This is as would be expected since there was no difference in the treatment (Morphine) applied to these groups. However, surprisingly, GEE analysis indicates group 3 was significantly ($P=0.024$) different to the other groups.

The naltrexone effect at Days 6, 8, and 10 was analyzed. All concentrations (above zero) of naltrexone were significantly different from zero naltrexone (group 1). All concentrations of naltrexone had a similar effect in increasing the latency period. Although 300 ng appeared to be most effective at enhancing latency, it was not significantly different from 30 or 3000 ng.

Group B

In a second series of experiments, 40 female mice were randomized into 5 groups of eight. All mice were administered single 3 mg/kg morphine daily (b.i.d.), beginning on Day 1. The anti-nociceptive effect was assayed by standard tail flick procedures for mice in Group 1 on Days 1, 3, 5, 8, 10 and 12. The mice in Groups 2–5 were assayed on Days 5, 8, 10 and 12. Groups 2, 3, 4 and 5 received daily doses of 3 ng/kg, 30 ng/kg, 300 ng/kg and 3000 ng/kg naltrexone (b.i.d.), respectively, beginning at day 6. Anti-nociceptive effect was assayed by tail flick on Days 5 (prior to naltrexone dosing), 6, 8, and 10.

The adaptation of mice in group 1 to the repeated daily dosing with morphine was analyzed. As with male mice, female mice show an adaptation to morphine especially from day five onwards. The change in latency within a day (day 1) of group 1 mice was analyzed. At all times after time zero latency was significantly longer than for time zero.

The variability between groups of mice were compared at Day 5. There were little differences between groups of female mice on day 5.

The naltrexone effect at Days 6, 8, and 10 was analyzed. All concentrations (above zero) of naltrexone were significantly different from zero in enhancing latency. In females, 30 ng appears to be significantly better than other concentrations at enhancing latency.

Group C

In a third series of experiments, 40 male mice were randomized into 5 groups of eight. All mice were administered single 3 mg/kg morphine daily (b.i.d.), beginning on Day 1. In addition, Groups 2, 3, 4 and 5 received daily doses of 3 ng/kg, 30 ng/kg, 300 ng/kg and 3000 ng/kg naltrexone (b.i.d.), respectively, beginning at day 1. The antinociceptive effect was assayed by standard tail flick procedures for all mice in on Days 1, 3, 5, 8, and 10. On Day 12, every mouse received a single bolus dose of 10 µg/kg naltrexone.

The naltrexone effect was measured at Days 1, 3, 5, 8 and 10. The enhancement of latency by naltrexone at 300 ng was significantly greater than other at concentrations (Table 14).

TABLE 14

Enhancement of Latency by Naltrexone in Male Mice

| Day | Group 1 | Group 2 | Group 3 | Group 4 | Group 5 |
|---|---|---|---|---|---|
| 1 | 9.3 | 13.3 | 12.4 | 16.3 | 13.5 |
| 3 | 6.2 | 7.5 | 9.3 | 17.1 | 13.0 |
| 5 | 1.6 | 4.5 | 7.5 | 11.8 | 12.0 |
| 8 | −2.3 | 5.5 | 7.1 | 9.4 | 10.4 |
| 10 | −3.3 | 2.7 | 3.2 | 6.1 | 7.4 |
| 12 | −4.3 | 1.1 | −0.8 | −0.2 | −0.7 |

Group D

In a final series of experiments, 40 female mice were randomized into 5 groups of eight. All mice were administered single 3 mg/kg morphine daily (b.i.d.), beginning on Day 1. In addition Groups 2, 3, 4 and 5 received daily doses of 3 ng/kg, 30 ng/kg, 300 ng/kg and 3000 ng/kg naltrexone (b.i.d.), respectively, beginning at day 1. The antinociceptive effect was assayed by standard tail flick procedures for all mice in on Days 1, 3, 5, 7, and 10. On Day 11, every mouse received a single bolus dose of 10 µg/kg naltrexone in addition to the existing morphine/naltrexone regimen.

The response to small doses of naltrexone was measured. Although a dose 0.3 ng/kg of naltrexone gave the longest latency, this was not significantly different from 0.03 or to 3 ng/kg of naltrexone (Table 13).

TABLE 13

Enhancement of Latency by Naltrexone in Female Mice

| Day | Group 1 | Group 2 | Group 3 | Group 4 | Group 5 |
|---|---|---|---|---|---|
| 1 | 5.4 | 12.2 | 12.4 | 15.0 | 12.3 |
| 3 | −0.1 | 11.0 | 10.7 | 10.3 | 9.6 |
| 5 | −4.1 | 4.3 | 6.9 | 1.9 | 3.4 |
| 7 | −5.0 | 6.1 | 2.4 | 0.2 | 1.9 |
| 10 | −3.3 | 4.4 | 9.3 | 5.9 | 6.7 |
| 11 | −5.2 | −1.0 | −0.7 | 0.8 | −0.7 |

Combined Analysis

Figure 6:
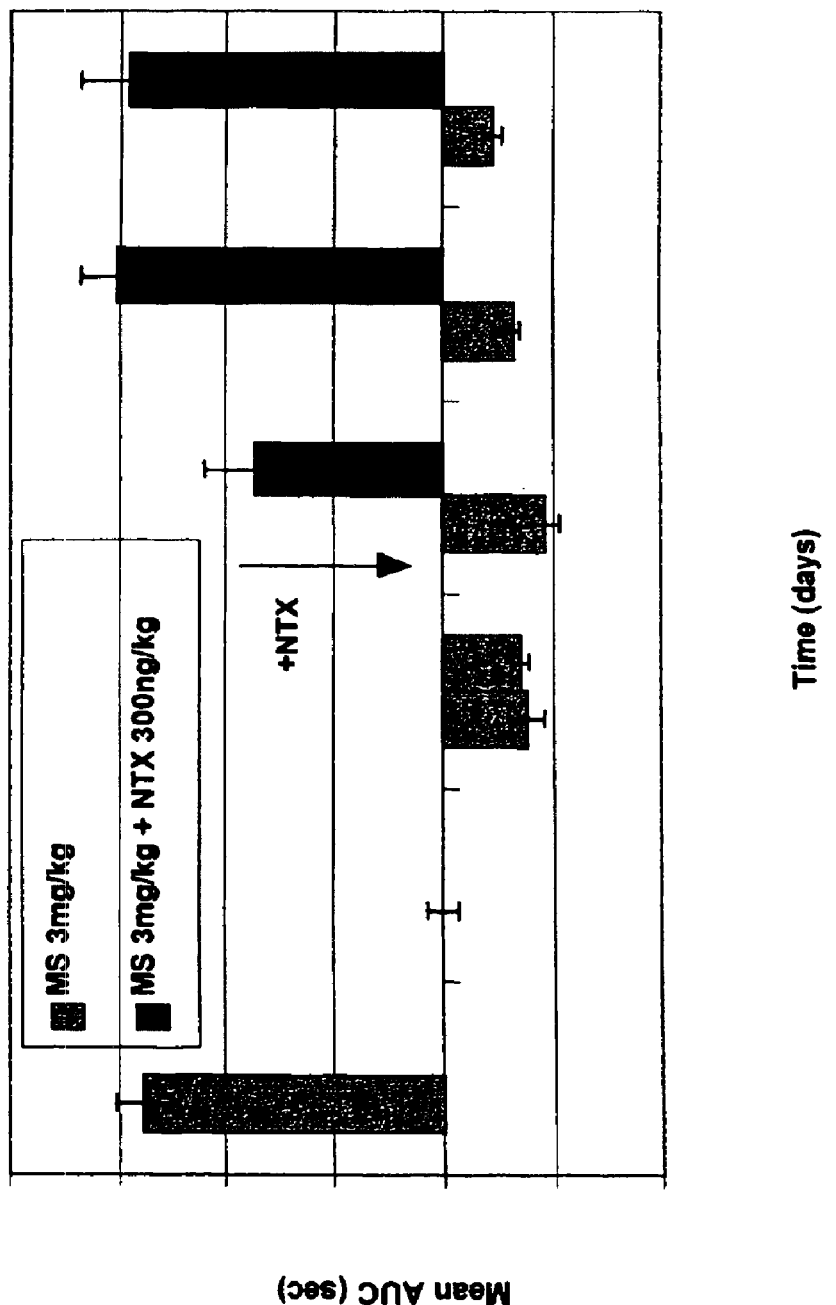
FIG. 6 illustrates that administration of naltrexone to morphine-tolerant mice breaks tolerance.

In an analysis of males and females combined (Groups A and B, on days 1, 3, 5, 6, 8 and 10), naltrexone at concentrations of 30 ng/kg and 300 ng/kg gave significantly longer latency than other concentrations of naltrexone (FIG. 6 and Table 15). In a combined analysis naltrexone administered to male mice (Groups A and C, on days 8 and 10), naltrexone at 300 ng gave the greatest latency and was significantly different to other concentrations of naltrexone.

TABLE 15

Enhancement of Latency by Naltrexone in Female Mice

| Day | Group 1 | Group 2 | Group 3 | Group 4 | Group 5 |
|---|---|---|---|---|---|
| 1 | 7.4 | 12.8 | 12.4 | 15.6 | 12.9 |
| 3 | 3.0 | 9.3 | 10.0 | 12.7 | 11.3 |
| 5 | −1.2 | 5.9 | 7.2 | 6.8 | 7.7 |
| 8 | −3.7 | 5.8 | 4.9 | 4.8 | 6.2 |
| 10 | −3.3 | 3.5 | 6.6 | 6.0 | 7.0 |

Figure 7:
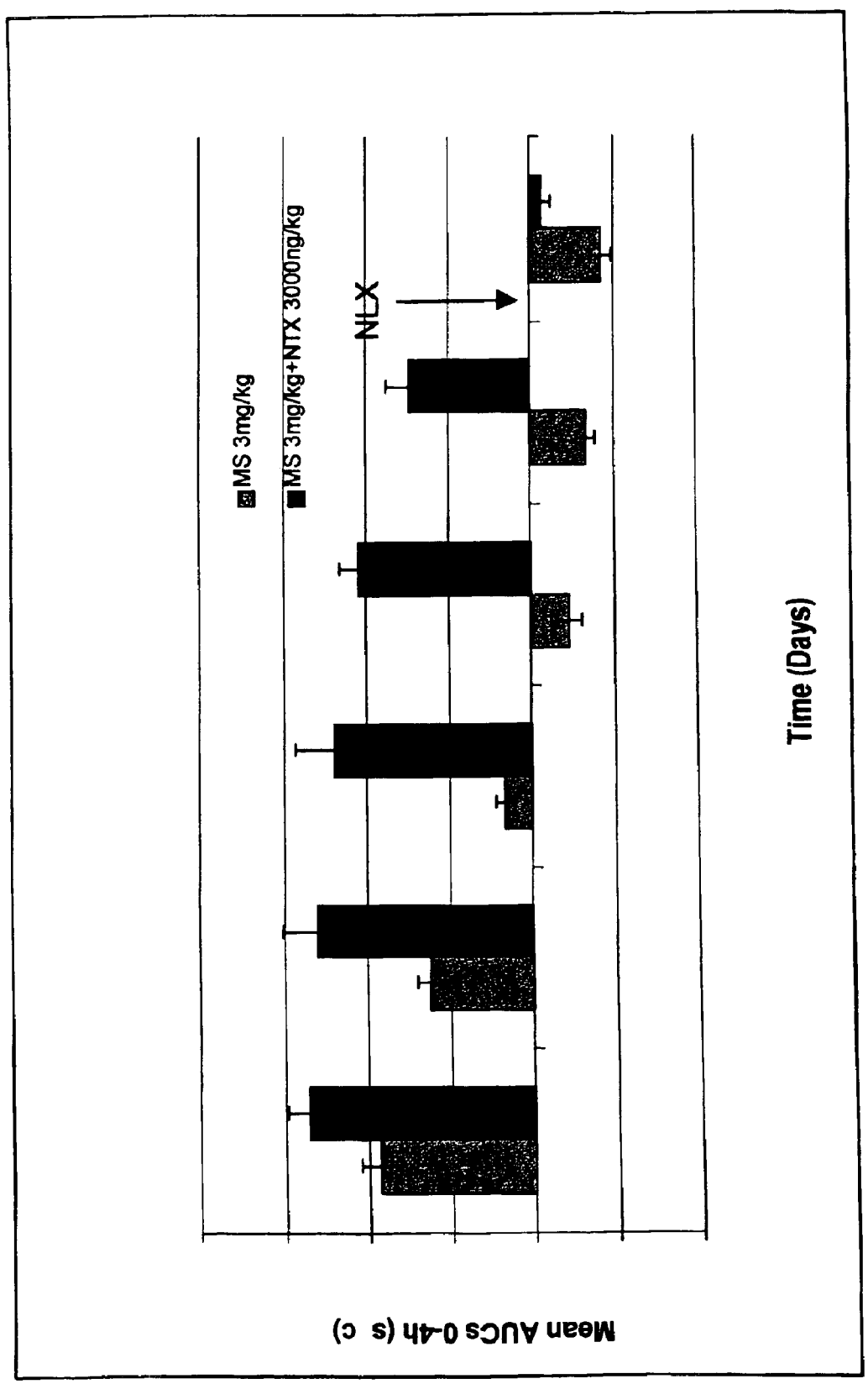
FIG. 7 illustrates that administration of naltrexone in combination with morphine prevents the mice from developing a tolerance to morphine.

3 mg/kg of morphine was administered as a single bolus dose to each mouse on group 1 on a daily basis. Mice in Group 2 were also administered 3 mg/kg morphine daily. In addition to the morphine, mice in Group 2 also received 3 ng/kg naltrexone daily beginning on Day 6. At Day 15, the dose of naltrexone was lowered to 0.1 ng/kg. By Day 5, the mice showed distinct tolerance to the morphine. However, administration of the naltrexone broke the tolerance (FIG. 7).

Results of parallel experiments using oxycodone in the place of morphine were comparable. For these experiments, male mice were administered 0.1 mg/kg oxycodone plus either 1 ng/kg naltrexone, 1 ng/kg nalmefene or 1 pg/kg of nor-BNI. In all cases the mice did not develop tolerance to the oxycodone. Similarly, female mice were administered either 1 mg/kg or 5 mg/kg oxycodone in combination with 1 pg/kg, 1 ng/kg or 1 µg/kg naltrexone or 1 pg/kg nor-BNI. None of the mice developed tolerance to the oxycodone. Additionally, the male and female mice who had developed a tolerance to oxycodone were administered a single 10 µg/kg dose of naloxone.

All publications and patent applications mentioned in this specification are herein incorporated by reference to the same extent as if each individual publication of patent application was specifically and individually indicated to be incorporated by reference.

The invention now being fully described, it will be apparent to one of ordinary skill in the art that many changes and modifications can be made thereto without departing from the spirit or scope of the appended claims.

I claim:

1. A composition comprising (a) a non-opioid CNS-active agent, wherein the said non-opioid CNS agent is selected from the group consisting of diazepam, lithium, triazolam, and zolpidem, and (b) an ABC drug transporter protein-inhibiting amount of an opioid inhibitor of an ABC drug transporter, wherein the amount is in the range of from 3 ng/kg to 3000 ng/kg.

2. The composition of claim 1, wherein the ABC drug transporter is a PGP drug transporter.

3. The composition of claim 2, wherein the PGP drug transporter is a PGP1a drug transporter.

4. The composition of claim 1, wherein the opioid inhibitor is an opioid receptor antagonist.

5. The composition of claim 4, wherein the opioid receptor antagonist is a compound of the formula:

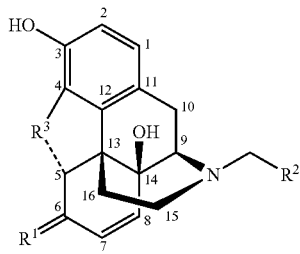

wherein $R^1$ is $CH_2$ or O;
wherein $R^2$ is a cycloalkyl, unsubstituted aromatic, alkyl or alkenyl; and
wherein $R^3$ is O, $CH_2$ or NH.

6. The composition of claim 4, wherein the opioid receptor antagonist is selected from the group consisting of naltrexone, naloxone, and nalmefene.

7. The composition of claim 1, wherein the inhibitor is a compound of the formula:

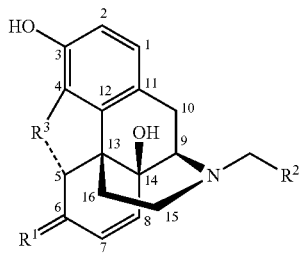

wherein $R^1$ is $CH_2$ or O;
wherein $R^2$ is a cycloalkyl, unsubstituted aromatic, alkyl or alkenyl; and
wherein $R^3$ is O, $CH_2$ or NH.

8. A composition comprising:
(a) a non-opioid CNS-active agent wherein the said non-opioid CNS agent is selected from the group consisting of diazepam, lithium, triazolam, and zolpidem, and
(b) an ABC drug transporter protein-inhibiting amount of an opioid receptor antagonist that is an inhibitor of an ABC drug transporter, wherein the amount is in the range of from 3 ng/kg to 3000 ng/kg;
wherein the composition is for the treatment of chronic pain, for controlling pain without dependence, tolerance, or withdrawal.

9. The composition of claim 8, wherein the opioid receptor antagonist is selected from the group consisting of naltrexone, naloxone, and nalmefene.

10. The composition of claim 8, wherein the opioid receptor antagonist is a compound of the formula:

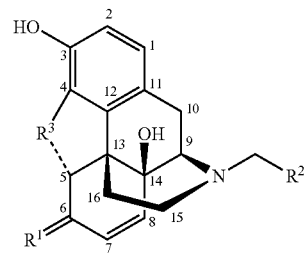

wherein $R^1$ is $CH_2$ or O;
wherein $R^2$ is a cycloalkyl, unsubstituted aromatic, alkyl or alkenyl; and
wherein $R^3$ is O, $CH_2$ or NH.

* * * * *